(12) United States Patent
Hetherington et al.

(10) Patent No.: US 12,123,929 B2
(45) Date of Patent: Oct. 22, 2024

(54) MINIMALLY COUPLED SHIM COILS

(71) Applicant: Resonance Research, Inc., Billerica, MA (US)

(72) Inventors: Hoby P. Hetherington, Wexford, PA (US); Kai-Ming Lo, Westford, MA (US); William F. B. Punchard, Woodstock (GB); Piotr M. Starewicz, Lexington, MA (US)

(73) Assignee: Resonance Research, Inc., Billerica, MA (US)

( * ) Notice: Subject to any disclaimer, the term of this patent is extended or adjusted under 35 U.S.C. 154(b) by 0 days.

(21) Appl. No.: 18/275,934

(22) PCT Filed: Feb. 7, 2022

(86) PCT No.: PCT/US2022/015482
§ 371 (c)(1),
(2) Date: Aug. 4, 2023

(87) PCT Pub. No.: WO2022/170186
PCT Pub. Date: Aug. 11, 2022

(65) Prior Publication Data
US 2024/0053418 A1    Feb. 15, 2024

Related U.S. Application Data

(60) Provisional application No. 63/146,995, filed on Feb. 8, 2021.

(51) Int. Cl.
*G01R 33/3875* (2006.01)
*A61B 5/055* (2006.01)
(Continued)

(52) U.S. Cl.
CPC ..... *G01R 33/3875* (2013.01); *G01R 33/3802* (2013.01); *A61B 5/055* (2013.01); *G01R 33/3858* (2013.01)

(58) Field of Classification Search
CPC ........... G01R 33/3875; G01R 33/3858; G01R 33/3802; A61B 5/055
See application file for complete search history.

(56) References Cited

U.S. PATENT DOCUMENTS

| | | |
|---|---|---|
| 2014/0302258 A1 | 10/2014 | Mathieu et al. |
| 2016/0054407 A1 | 2/2016 | Parizh et al. |

(Continued)

FOREIGN PATENT DOCUMENTS

KR    101932070 B1    12/2018

OTHER PUBLICATIONS

International Search Report and Written Opinion in Application No. PCT/US2022/015482 dated May 30, 2022 (10 pages).

*Primary Examiner* — Rishi R Patel
(74) *Attorney, Agent, or Firm* — BURNS & LEVINSON LLP

(57) ABSTRACT

The present invention provides a method for structurally designing that article of manufacture and a constructed and operational article of manufacture that will allow the inclusion of minimally coupled higher order/degree shim coils in any magnetic resonance apparatus. The novel system and methodology includes determining the shim coil terminal voltage without any prior or advance knowledge of the configuration of the electrical windings of the imaging gradient coil that is inducing that voltage.

20 Claims, 8 Drawing Sheets

(51) Int. Cl.
    *G01R 33/38*     (2006.01)
    *G01R 33/385*     (2006.01)

(56) References Cited

U.S. PATENT DOCUMENTS

| | | |
|---|---|---|
| 2016/0252594 A1 | 9/2016 | Biber |
| 2020/0393526 A1 | 12/2020 | Wang |
| 2021/0048494 A1* | 2/2021 | Bindseil ................ G06F 30/10 |

* cited by examiner

SEGMENT OF SHIM COIL EXTENDING FROM
$Z0_1$ TO $Z0_2$ AXIALLY AND COMPRISING 2m SADDLES
AZIMUTHALLY BETWEEN 0 AND $2\pi$

THE DISTRIBUTION OF TURNS AZIMUTHALLY
IS PROPORTIONAL TO $COS(m\phi_0)$

THE DISTRIBUTION OF TURN
COMPONENTS AXIALLY IS PROPORTIONAL TO $$\text{SIN}\left[\frac{(z_0 - z_{01})}{(z_{02} - z_{01})} j\pi\right]$$

SUM OF ALL TURN COMPONENTS $n(z_0) = \sum_{j=1}^{jmax} n_j(z_0)$

WITH $n_j(z_0)$ NORMALIZED SUCH THAT $n(z_0)\big|_{max} = 1$

ELEMENTAL LOOP OF n TURNS ENCLOSING AREA dA PENETRATED BY TIME DEPENDENT MAGNETIC FIELD $\dot{B}_\perp$ PERPENDICULAR TO LOOP

RADIAL FIELD PENETRATING ELEMENT OF SADDLE COIL WOUND ON SURFACE OF CYLINDER

Minimally Coupled Z2X Shim Turns Distribution

MINIMALLY COUPLED SHIM COILS

CROSS-REFERENCE TO RELATED APPLICATIONS

This application is a U.S. national phase entry under 35 USC § 371 of Patent Cooperation Treaty Application No. PCT/US2022/015482 filed Feb. 7, 2022, which in turn claims priority to U.S. Provisional Patent Application No. 63/146,995 filed Feb. 8, 2021. Each of the above-described applications is hereby incorporated herein by reference in their entirety.

BACKGROUND OF THE INVENTION

A Typical Magnetic Resonance System:

Magnetic resonance ('MR') systems employ a spatially uniform and temporally constant main $B_0$ magnetic field. For the purpose of excitation of nuclear spin magnetization within the examination volume of the magnetic resonance device, a radio frequency pulse sequence, the $B_1$ field, is superimposed perpendicular to the $B_0$ field at the appropriate resonant frequency.

Magnetic resonance imaging devices also conventionally include a set three of gradient coils for the generation of the linear gradient magnetic fields, by which spatial encoding of the nuclear spin magnetization is achieved. During the magnetic resonance procedure, pulse sequences (consisting of radio frequency and switched gradient magnetic fields) are applied to a targeted subject (such as a live patient) to generate magnetic resonance signals, which are detected and stored to obtain information subsequently used to reconstruct spectra and images of the object. These procedures determine the characteristics of the reconstructed spectra and images such as location and orientation in the targeted subject, dimensions, resolution and contrast. The operator of the magnetic resonance device typically selects the appropriate sequence and adjusts and optimizes its parameters for the particular application.

The existence of a strong and homogeneous magnetic field is very important for magnetic resonance. A major requirement for the static magnetic field in magnetic resonance systems is that it must be substantially homogeneous over the desired ROI. Typically therefore, for whole body magnetic resonance systems, the magnetic field should not deviate from the central value by more than about 5 ppm over a spherical imaging volume having a diameter of 45 cm to 50 cm.

The superconducting magnets used in conventional medical magnetic resonance systems are typically about 1.6 m to 2.0 m in length and have clear bores of diameter in the range of 0.8 m to 1.0 m. The magnet is traditionally symmetric in construction, the midpoint of the bore volume being located at the geometric center of the magnet's structure.

The magnet generating the $B_0$ field is designed such that the magnetic field that it produces meets the stringent field homogeneity specifications. However, because of manufacturing tolerance issues, the conductor is never placed in exactly in the positions called for by the design. Because of such defects, the homogeneity of the as-built magnet does not meet the field homogeneity design specifications; and the $B_0$ field contains inhomogeneity components that adversely affect the quality of the images and spectra that are acquired. Typical magnetic resonance imaging devices therefore include some form of shimming means for improving and controlling the homogeneity of the $B_0$ field.

An illustration of the basic components for a typical superconducting magnet system appears in Prior Art FIG. 1A. As seen therein, the superconducting magnet system 10 includes a magnet housing 12, a superconducting magnet 13 with solenoidal windings whose axis of symmetry by convention is the Z-axis of a Cartesian coordinate system, shim coils 14, gradient coils 16, RF coils 18, and a patient table 20.

As is well known in the art, the superconducting magnet 13 produces a substantially uniform magnetic $B_0$ field within its design FOV. This $B_0$ field is directed along the positive Z-axis. Such systems are useful for performing magnetic resonance investigations and are suitable for producing diagnostic images for human studies; similar systems can be used for spectral analysis applications.

In such systems there are traditionally three pulsed gradient coils: the X-gradient coil, the Y-gradient coil, and the Z-gradient coil, each of which generates a magnetic field in a direction the same as that of the $B_0$ field, the Z axis direction. However, in contrast to the $B_0$ field which is uniform, the field generated by each gradient coil varies linearly in one of three orthogonal directions. The X-, Y- and Z-gradient coils generate respectively a Bz component of field that varies linearly in the X, Y and Z axis directions. The magnetic fields generated by these coils provide the means for correlating received signal with location of origin within the subject being imaged.

Typically, the Z-gradient coil is solenoidal and comprises a wire conductor wound circumferentially on the surface of a cylinder, a winding geometry similar to that of the magnet generating the $B_0$ field. In contrast, the X-gradient coil conventionally has the topology of a saddle mounted on a cylinder. The Y-gradient coil is identical to the X-gradient coil, but is rotated azimuthally by 90°. The conductor for the X- and Y-gradient coils may be made of wire or of copper plate, in which case the turns are formed either by machining or by chemically etching away the copper between turns.

Note also that the X-, Y- and Z-gradient coils are mounted concentrically. To minimize the generation of eddy currents induced in conductive components of the cryostat, there are three so-called gradient shields, one for each of the gradient coils. These have a topology which is the same as that of their associated coils and are located at larger radii. The currents in these shields are in a direction opposite to that of the coils and are distributed in such a way as to minimize the magnetic flux which extends outside of the shields. Both the coils and shields are resistive and operated close to room temperature. Also, they are typically water cooled because of the energy deposited in them by the high current pulses from current regulated, high voltage amplifiers.

Other features of the traditional magnetic resonance system are illustrated by Prior Art FIGS. 1B and 1C respectively. As shown in Prior Art FIG. 1B, the targeted subject 25 is to be placed in the middle of the main magnetic field $B_0$ generated by the superconducting magnet 13. The voltage measurements are registered by measurement circuitry 40. Voltage measurements are used to reconstruct images and the images are displayed on a display 50. Preferably, the application of current is synchronized with the magnetic resonance imaging sequence from a magnetic resonance imaging system 60. A greater detailing of functions is set for by Prior Art FIG. 1C.

Thus, the basic hardware components of all high field strength MR systems conventionally are: the superconducting magnet which produces a stable and very intense magnetic field; the gradient coils which create a variable field to enable spatial encoding; and the radio frequency (RF) coils which are used to stimulate transitions between the energy states of the nuclei. A computer controls the scanning procedure and processes the information.

In addition, the range of magnetic field strengths typically used for clinical in-vivo imaging in superconductive solenoidal magnets is from about 0.5 T to 3.0 T. Open structure magnets usually have a magnetic field strength in the range from about 0.2 T to 1.2 T.

The Generated Magnetic Field:

A conventional magnetic resonance imaging/spectroscopy system, of which the system illustrated in Prior Art FIG. 1A and FIG. 1B is a typical example, generates a substantially homogeneous and temporally constant (or static) main magnetic field, commonly referred to as the $B_0$ field (also termed the 'basic magnetic field') in a limited spatial volume (also called an 'examination volume' or an 'imaging volume' or the 'field of view') within which the targeted subject is disposed.

Typically, this $B_0$ field exists in the same direction as, and is parallel to, the positive Z-axis of a Cartesian coordinate system within this examination volume. Consequently, the plane which is perpendicular to the $B_0$ field lines is the XY plane, the X-axis extending horizontally and the Y-axis extending vertically. For clarity, see Prior Art FIG. 1B where the direction of the $B_0$ magnetic field is indicated and corresponds to the direction of the positive Z-axis.

Imperfections in the Primary Magnetic Field:

Inhomogeneities arise from misplacement of windings during manufacture, by environmental effects, and from the presence of the target to be imaged. Of these, the last is the most difficult to deal with and to resolve.

(a) For technical and economic reasons, the high-field high-homogeneity magnets suitable for MRI and MRS applications of necessity use windings made of material that is a superconductor. This requires that the magnet be maintained at a safe margin below the critical temperature of the particular superconductor material used; and typically such magnets operate at about 4K. As the magnet is cooled from room temperature to 4K, the windings and the magnet structure physically contract such that the cold temperature dimensions are meaningfully different from those existing at room temperature.

Furthermore, when the magnet is energized, the interaction of the current in the coil (with the magnetic field that it generates) creates what are known as 'Lorentz forces' on the conductor. These are transmitted to the coil forms and support structure for the magnet. Such Lorentz forces put the magnet components under mechanical stress, which in turn results in strain that creates additional misplacement of the windings.

To a large extent, the dimensional changes due to cool down and magnet energization can be predicted; and the magnet is designed in such a way that, after cool down and energization, the windings are in a position which creates the desired field homogeneity. Thus for a well-designed magnet, this not a major source of field inhomogeneity.

(b) Of far more serious concern are deviations in the placement of conductor from the ideal positions required by the design. For example, the theoretical design of the magnet assumes that the windings consist of conductors that are ideal hoops. In practice however, the conductor is continuous; and during magnet fabrication, the wire not only must make a transition from one turn to another every 360 degrees, but also must make a transition from one layer to the next at the end of each layer. This results in the presence of axial and radial components of current, which in turn, generate fields which deviate from the field configuration as designed.

Furthermore, high homogeneity magnet systems of necessity comprise more than one set of windings, i.e., they are multi-coil systems and conductor must be routed from one coil to the next. Even though, to ensure cancellation, every attempt is made to run wires carrying opposite currents in pairs, inevitably there are regions where the pairing is not exact. This too generates spurious field configurations. Mechanisms such as these, which result in deviations from the ideal placement of conductor, are responsible for creating many magnetic field inhomogeneities.

(c) Another source of inhomogeneity arises from the surroundings of the magnet. If there is ferromagnetic material in the vicinity, for example steel reinforcement in the concrete foundation or steel beams in the walls or ceiling of the room in which the magnet is located, then it will become magnetized. This magnetized material produces its own magnetic field which is then superimposed on that of the magnet, thereby degrading it.

Inhomogeneities such as these are due entirely to the magnet hardware or the environment in which the magnet is situated; and once the magnet is installed and energized, they are constant. When a MRI magnet is commissioned, it typically undergoes an initial shimming procedure for minimizing such effects by means of passive shims, (ferromagnetic elements placed in the bore of the magnet). In some rare cases, low order, low degree integrated superconducting (SC) shims are used, but only a small fraction of commercially produced magnets contain SC for performing this task.

(d) A more challenging class of inhomogeneities arises from the interaction of the $B_0$ field with biological tissue that is to be imaged. Any substance that is placed in an external magnetic field has an additional field induced in.

In a linear isotropic material, the induced field is proportional to the applied field and the constant of proportionality is known as the magnetic susceptibility, X. Thus, an object placed in an applied field $B_0$ will experience an induced field $\delta B_0 = X B_0$.

If the susceptibility of the specimen being examined were constant throughout its volume then there would be a uniform field shift throughout the specimen; only the magnitude of $B_0$ would change. However, biological specimens contain cavities and organs with cells consisting of substances with a multitude of different susceptibilities which change across cell and organ boundaries.

Biological tissue has a susceptibility of the order of −10 ppm, whereas air has a susceptibility of about +0.3 ppm. The difference in susceptibility between brain white matter and grey matter is about 0.02 ppm. This means the field strength can change by parts per million on small spatial scales. This is equivalent to saying that the nature of the inhomogeneity is of high order and degree and that it can be corrected only by high order and degree shimming.

An additional complication arises from the fact that significant differences in anatomical detail are observed in the same organ, e.g., the human brain, in different individuals. The differences are large enough that inhomogeneity corrections have to be applied on a subject by subject basis; in a clinical environment the magnet must be reshimmed between patients.

Inhomogeneities associated with this mechanism give rise to what are known as susceptibility artifacts; and it should be noted that because of the proportionality of the induced field to the applied field, the magnitude of the induced field which has to be corrected increases with increasing applied field. Thus, the magnitude of the field to be corrected at 3.0 T and 7.0 T is respectively 2.0 times and 4.7 times that at 1.5 T. This illustrates the importance of high order and degree shimming for correcting susceptibility artifacts arising in biological tissue when using high field MRI/MRS systems; and the fact that as the ambient magnetic field is increased, the strengths of the shims necessary for field correction must be proportionately increased.

Correction of Inhomogeneities:

The interior magnetic field distribution of the primary magnet can be decomposed into a set of orthogonal functions known as interior spherical harmonics. Each one of these functions is the product of a circular function specifying the azimuthal angular position of the field point, an associated Legendre function specifying its polar angular position, and the power of a polar radius that specifies its distance measured from the center of the magnet.

Each spherical harmonic is characterized by a unique spatial field distribution. The fundamental spherical harmonic is the ideal desired magnetic field distribution. Higher field harmonics constitute impurities that make the primary magnetic field inhomogeneous. An analysis of a map of an unshimmed magnetic field reveals the strengths of a number of these field harmonics. See Appendix I included hereinafter entitled "Principles of Field Correction" for a far more detailed explanation.

The Problems With Conventional Shim Coil Correction Systems:

To make imaging possible, the primary magnetic field must be very homogeneous; and to achieve this, another set of coils—typically known as shim coils—is utilized. Some shim coils may be superconducting and these are positioned in the cryostat that contains the primary magnet; but most shim coils conventionally operate at room temperature and are either physically intimately associated with the pulsed gradient coils or are located outside the gradient coils. It is beneficial to bring the shim coils relatively close to the patient in order to decrease the power requirements. The purpose of shim coils is to compensate for imperfections existing in the primary magnetic field.

Traditionally, the shimming system of an NMR magnet typically is formed of a number of individual shim coils. Typically five shim coils are used collectively to generate a correcting magnetic field that corresponds to a specific term of a spherical function expansion of the second order of the primary magnetic field. These five terms or field terms are typically explicitly determined by a magnetic field measurement so that each shim coil can be correspondingly adjusted such that the correcting magnetic field generated by each shim coil neutralizes and cancels out the respective term-related inhomogeneity.

It is recognized however that each one of these shim coils in the system is designed to generate a magnetic field distribution/correction corresponding substantially to only one spherical harmonic, and each shim coil is energized individually and independently of the others. Thus, if the strengths of the spherical harmonic distortions then present in the unshimmed magnetic field are known, then the current (amperage) applied to each one of the shim coils in the system can be individually adjusted in such a way that an appropriate field correction—equal in magnitude but opposite in sign—is created to neutralize the corresponding impurity present in the primary magnetic field. In this manner, this shimming procedure cancels the strength of the various impurities and results in the formation of a more homogeneous primary field.

Because there is a mutual inductance between the shim coils and the pulsed gradient coils, during the time that the field due to the pulsed gradient coils is changing, an electric field is induced in the shim coils. Depending on the relationship between the symmetry (i.e., the spatial distribution of the windings), of each one of the pulsed gradient coils and each one of the shim coils, a net voltage may or may not appear across the terminals of any shim coil. Also, because of the mutual inductive coupling effect, there will always be a distribution of induced voltages appearing within the windings of a shim coil. However, for most shim coils, equal magnitudes of positive and negative voltage are induced internally, and consequently the net voltage that appears across the terminals of a shim coil is substantially zero.

One additional point of information must be clearly understood. It can be shown that a pulsed Z-gradient coil which has solenoidal azimuthal current symmetry cannot induce net voltages in any shim coil that has azimuthal current symmetry that is of the form $\cos(m\varphi)$. Rather, a pulsed Z-gradient coil which has solenoidal azimuthal current symmetry can induce net voltages only in coils that have a corresponding solenoidal azimuthal symmetry. Furthermore, a pulsed Z-gradient coil which has solenoidal azimuthal current symmetry can induce voltages only in coils of the same azimuthal symmetry that have the same current anti-symmetry about the mid-plane. Thus, the Z1 pulsed gradient coil will induce non-zero terminal voltages in such shim coils as Z3, Z5, etc—but not in a ZX shim coil.

Similarly, an X ($\cos(\varphi)$ azimuthal symmetry) or a Y ($\sin(\varphi)$ azimuthal symmetry) pulsed gradient coil cannot induce any net terminal voltage in any shim coil having solenoidal azimuthal symmetry. Pulsed X-gradient coils are similarly non-interactive with any member of the $\sin(\varphi)$ shim coil family and vice versa.

Within the $\cos(\varphi)$ family, only shim coils with current symmetry across the mid-plane corresponding to that of the pulsed X-gradient coil will have a non-zero induced terminal voltage. This means that voltages will appear across the terminals of such shim coils as Z2X, Z4X, etc. Similar effects apply to the $\sin(\varphi)$ family.

Consequently, the affected shim coils of most importance then are the third degree shims, Z3, Z2X and Z2Y, since, for magnetic resonance imaging or magnet resonance spectroscopy applications, these are essential for ensuring high quality results. This is particularly true for high field, i.e. 3T and above, MR applications involving neuro-imaging.

The Recurring High Voltages Problem:

The problem associated with high voltages appearing at the terminals of shim coils concerns the effect that they have on the power supplies controlling the current in the shim coils. For example, estimates of the voltages appearing across the terminals of individual Z3, Z2X and Z2Y shim coils (suitable for imaging human heads) indicate that the voltages can be in excess of 500 V. Such voltages are well beyond the voltage compliance of the shim amplifiers controlling the current in these shim coils; and the requisite and necessary control over field homogeneity provided by these shim coils would be temporarily lost with consequent image degradation.

It is particularly noted that, because of the severe restrictions concerning the spatial locations where shim coils can be tangibly positioned, the shim coils and the shimming system as a whole would inevitably be subject to the changing magnetic fields of the pulsed imaging gradients, and their wire windings would experience many induced electric fields. The resultant induced high voltages that appear internally might be accommodated by ensuring that individual coil sections are adequately insulated from one another, but high voltages that appear at the terminals of any discrete shim coil will have an adverse effect on the operation and control of the associated shim amplifier.

Note also that shim coils that create magnetic fields with azimuthal symmetry different from the pulsed imaging gradients, or shim coils that create magnetic fields which have symmetry different across the mid-plane from the pulsed imaging gradients, do not experience net induced terminal voltages. All third degree shim coils except shims Z2X, Z2Y and Z3 respectively fall into this category.

Consequently, to date there has been no practical solution to the problem of the high induced terminal voltages routinely present on the Z2X, Z2Y and Z3 shims, and therefore these particular shim coils are rarely employed and are not commonly present as part of conventional shim coil sets and shimming systems. In all cases, when used, the coils are positioned outside of the gradient coil shield, rendering them quite inefficient.

SUMMARY OF THE INVENTION

The purpose and value of the present invention is to provide an article of manufacture and a method for structurally designing that article of manufacture that will allow the inclusion of minimally coupled higher order/degree shim coils in any magnetic resonance apparatus. Accordingly, the present invention provides all of the following:

(1) A method for calculating the magnitude of the induced voltage distribution in any shim coil that is located within the central region of a pulsed gradient coil without having any knowledge of the details of construction or the distribution of windings in that pulsed gradient coil.

(2) A method for designing a shim coil that can be located within the central region of any pulsed gradient coil such that the voltage that is induced across its terminals by the field due to that imaging gradient coil is less than the voltage compliance limit of its associated shim amplifier, that voltage compliance limit typically being 50 V.

(3) A method for fabricating a shim coil capable of substantially reducing the inductive coupling occurring in an MR assembly between the pulsed imaging gradient coils and an in-bore positioned shim coil having the same symmetry as the gradient coils.

The novel method employs a specific formula by which the terminal voltage of the fabricated shim coil can be calculated without any prior or advance knowledge of the configuration of the electrical windings of the imaging gradient coil that is inducing that voltage.

This specific methodology is stated in terms of precise parameters which collectively define the location and the structural configuration of the windings for the shim coil, wherein these parameters include:

the number of axially disposed modules comprising the shim coil.

And for each module, the axial and radial coordinates defining its position,
the number of turns that it contains and
the features defining the azimuthal and axial distribution of those turns.

It is noted also that the described method is an adaptation and modification of well-known conventional procedures for constrained optimization of functions, the details of which are disclosed in detail and referenced herein. The present modified procedure, which makes use of the novel methodology for calculating induced voltage, provides the manufacturer or user with an appropriate set of shim coil design parameters which collectively define the location and the constrained configuration of the windings for the shim coil structure. The result is an operational and highly practical shim coil structure in which the voltage induced across its terminals is constrained to be less than a desired value, such as the voltage compliance limit of the shim coil's associated amplifier.

(4) A fabricated portable shim coil insert structure which demonstrates a substantially reduced inductive coupling when used with a set of pulsed imaging gradient coils then permanently arranged around the periphery of the bore of an MRI magnet in an MRI assembly.

The present invention thus provides a fabricated article of manufacture comprising at least one operative shim coil structure which can be placed in a desired location and is operative in that self-chosen location such that the induced voltage due to a pulsing imaging gradient coil that appears across its terminals is less than the voltage compliance limit of the shim amplifier associated with that shim coil, typically far less than 50 volts.

Overall therefore, it will be appreciated that the use of higher degree shim coils having these capabilities will substantially improve the quality of all MR images generally (and particularly images of human heads in magnetic resonance assemblies operating at magnetic field strengths of 3T and above). Thus, the present invention can be effectively utilized in at least two different physical formats:

(i) As original equipment manufactured (OEM) component present in newly constructed MR assemblies; and (ii) As a portable discrete set of shim coils which can be retroactively fitted and placed into an existing and presently operative MR apparatus.

In both of these use instances, the present invention will improve the efficacy of high strength magnetic field MR imagers; be of great benefit to public health; and provide a significant improvement in many medical applications.

BRIEF DESCRIPTION OF THE DRAWING

The present invention can be more easily understood and better appreciated when taken in conjunction with the accompanying Drawing, in which.

Prior Art

Prior Art

Prior Art

Figure 6:
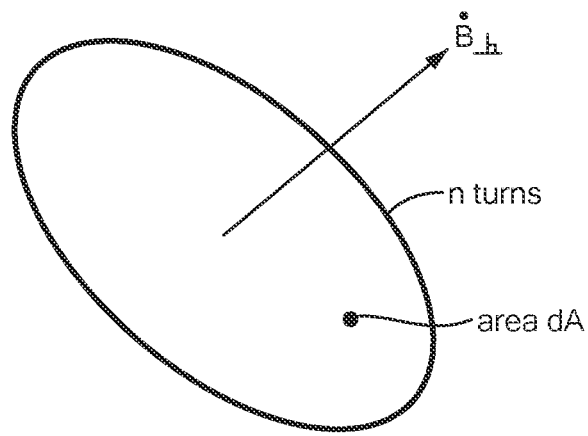
Figure 7:
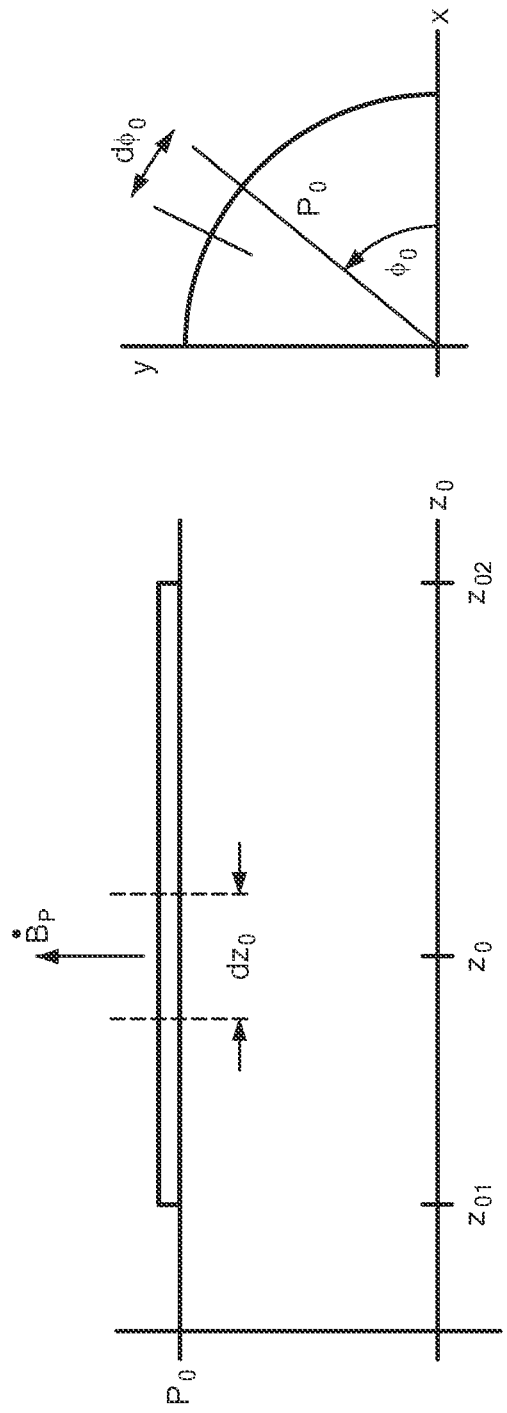
Figure 8:
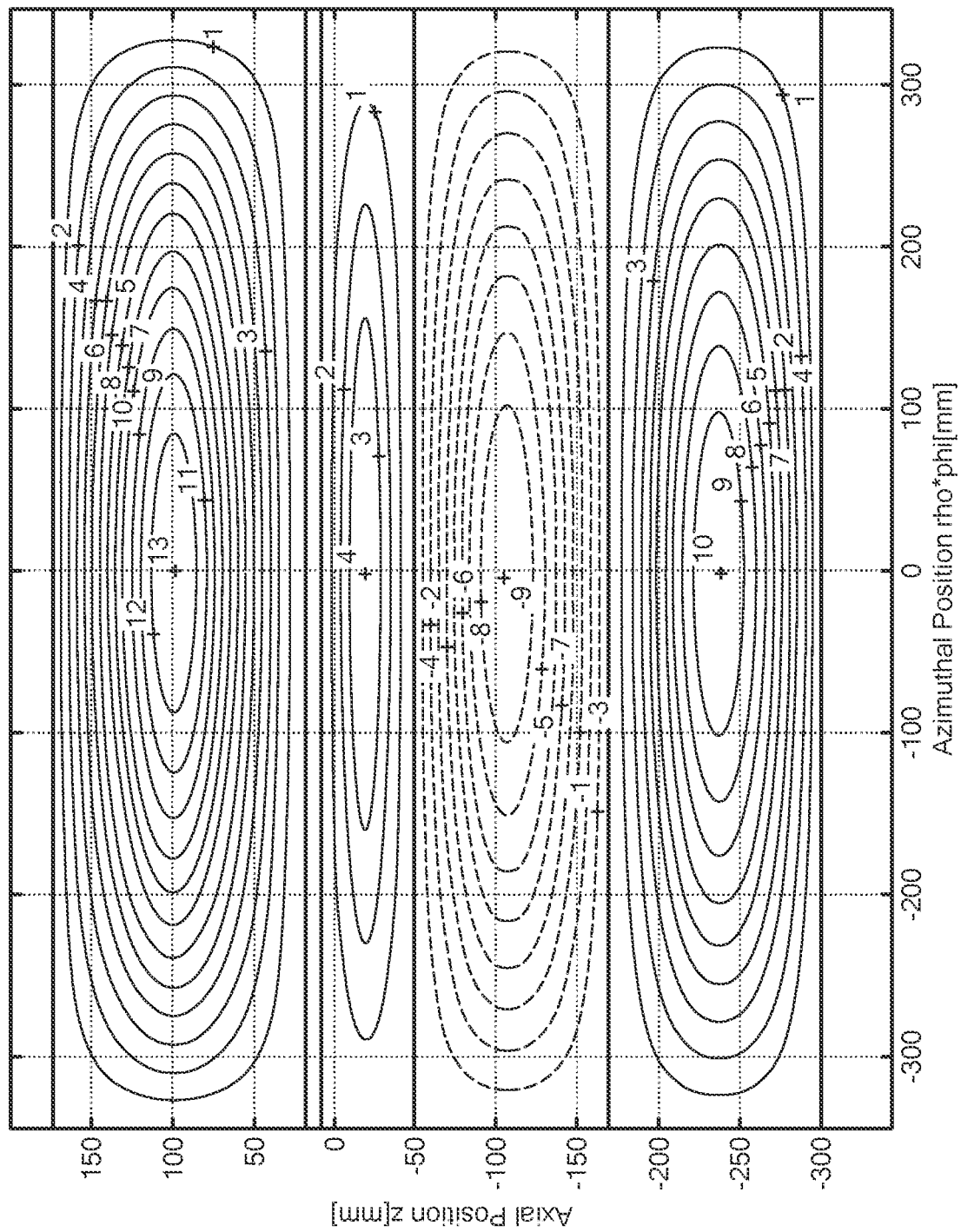

with $nj(z_0)$ normalized such that $n(z_0)|_{max}=1$;

FIG. 6 is an illustration showing an elemental loop of n turns enclosing area dA penetrated by time dependent magnetic field $B_\perp$ perpendicular to loop;

FIG. 7 is an illustration showing a radial field penetrating an element of a saddle coil wound on the surface of a cylinder; and FIG. 8 is a graph showing a 180 degree segment of a minimally coupled Z2X shim turns distribution.

DETAILED DESCRIPTION OF THE INVENTION

Perspectives:

Unless steps are taken to prevent it, a shim coil that has azimuthal symmetry and symmetry about the mid-plane corresponding to that of any pulsed imaging gradient coil will experience a net voltage across its terminals when exposed to the changing field of that imaging gradient coil. A shim amplifier that controls the current in its associated shim coil is connected to those terminals and hence experiences the same induced voltage. If that voltage exceeds a certain value, typically referred to as the compliance voltage—then at best the shim amplifier will lose control of the current, and at worst will be damaged.

Table 1 below presents a partial list of imaging coils and the conventionally built shim coils with which they interact in such a way that a net voltage appears across the terminals of the shim coils.

TABLE 1

| Linear Imaging Gradient Coils | Z | X | Y |
|---|---|---|---|
| Associated Shim Coils | Z* | X* | Y* |
| (which experience a | Z3 | Z2X | Z2Y |
| net terminal voltage) | Z5 | Z4X | Z4Y |
| | etc. | etc. | etc. |

(*Typically not present.)

(a) Linear imaging gradient coils are those which have been and are routinely used in both clinical and research applications. These linear imaging coils generate fields whose strength is substantially directly proportional to the distance from the origin along the direction indicated by the name of the gradient that they produce.

(b) Non-linear gradient coils are those which are used in an experimental imaging technique which presently is in the research and development stage. The use of such non-linear gradient coils and experimental imaging technique offers some potential advantages over conventionally known imaging procedures using linear gradient coils; and if this promise is fulfilled, then nonlinear imaging techniques may in the future be used in a clinical environment.

As their name suggests, the strengths of the fields that non-linear gradient coils produce varies in a nonlinear manner as the distance from the origin increases. Presently, research groups are conducting on-going investigations using Z2, C2 and S2 nonlinear gradients; but in principle, there is no reason why any other type of nonlinear gradient should be excluded.

The strength of the field generated by these second degree shim coils is proportional to the square of the distance from the origin along a polar radius. Thus, for those nonlinear gradients presently being used in research applications, we have the following as listed by Table 2 below.

TABLE 2

| Non-Linear Imaging Gradient Coils | Z2 | C2 | S2 |
|---|---|---|---|
| Associated Shim Coils | Z2 | C2 | S2 |
| (which experience a | Z4 | Z2C2 | Z2S2 |
| net terminal voltage) | Z6 | Z4C2 | Z4S2 |
| | etc. | etc. | etc. |

The list presented by Table 2 can be extended indefinitely. For further information concerning nonlinear gradients see the following representative publications: "Parallel imaging in non-bijective, curvilinear magnetic field gradients: a concept study", Hennig J, Welz A M, Schultz G, Korvink J, Liu Z, Speck O, Zaitsev, *M. MAGMA*, 2008 March 21(1-2):5-14; "O-space imaging: Highly efficient parallel imaging using second-order nonlinear fields as encoding gradients with no phase encoding", Stockman J P, Ciris P A, Galiana G, Tam L, Constable R T, *Magn Reson Med* 2010, August: 64(2):447-456; and "Simultaneously driven linear and non-linear spatial encoding fields in MRI", Gallichan D, Cocosco C A, Dewdney A, Schultz G, Hennig J, Zaitsev, *M. Magn Reson Med* 2011, March: 65(3):702-714, each of which is hereby incorporated by reference herein in its entirety.

I. The Shim Coil Structural Designs

As per the present invention, the structure of a shim coil can be designed in such a way that the imaging gradient coil with which it is associated will induce a voltage across the shim coil's terminals that is limited to any desired value—i.e., the associated shim coil is inductively substantially decoupled from the imaging gradient coil. This decoupling effect is achieved by ensuring that the mutual inductance between the imaging gradient coil and its associated shim coil is substantially reduced. However, a structural shim coil design of this kind is possible only if the positions of the electrical windings of the corresponding imaging gradient coil are known. Unfortunately, such information is usually available only to the manufacturer of the imaging gradient coil. Hence, the procedure for causing a marked reduction of mutual inductance is not generally applicable.

The present invention presents and provides a novel and unique alternative method and structural practice for designing shim coils that inductively are substantially decoupled from their corresponding imaging gradient coils. In this particular method and structural practice, prior advance knowledge of the positions of the electrical windings of the associated imaging gradient coils is not required and so the procedure for causing a marked reduction of mutual inductance is generally applicable for all corresponding imaging gradient coils without limitation. In particular, the unique method and structural practice is applicable for shim coils that are to be located within the central region of the imaging gradient coils. Thus, it is not only now possible, but also is appropriate to include a plurality of such decoupled shim coils as co-members as a set of discrete shims in a shim coil insert whose purpose is to enhance the quality of MR images (by providing higher degree harmonic compensation). The resulting shim coil insert comprises several separate structural components disposed axially.

Accordingly, the present invention also comprises a general-purpose and retrofittable shim coil insert which is suitable for use in existing MR scanners, thereby eliminating the need for major hardware modifications, and being very beneficial for its capability to increase the technical accuracy and precision of the previously existing installed MR apparatus. As an easily insertable in-bore shim coil insert capable of accommodating modern RF head coils which include multi-transmitter arrays, the invention is compliant with the standard shim amplifier technology; and this makes the unique article of manufacture an economically viable choice and addition for achieving the highest level of performance without compromising the functionality of the existing MR scanner for other applications. Another major advantage of the present invention is that the retrofittable shim coil insert offers a markedly extended life span for very costly MR equipment and provides operating parameters not possible with any modern MR scanner to date.

II. The Underlying Theory and Structural Basis of the Present Invention

For typical linear gradients, the application of higher degree shims can significantly improve the quality of MR images of human heads in MR imagers with field strengths of 3T and above. If a set of such shims were to be retroactively fitted into and used in a presently existing MR imaging assembly, the shim coil insert would improve the magnetic field homogeneity and efficacy of a large number of existing high field MR imagers, and thereby provide a significant opportunity for improving magnetic resonance imaging.

Also, because of the severe restrictions on where such shims can be located in the MR apparatus, any shim coil would inevitably be subject to the changing magnetic fields of the pulsed imaging gradients; and their shim coil windings would experience induced electric fields and high voltages often exceeding 500 volts. The resultant induced high voltages that appear internally might be accommodated by ensuring that individual shim coil sections are adequately insulated from one another; but the high voltages that will exist at the terminals of any shim coil will always have an adverse effect on the operation of the associated shim amplifier.

In addition, one must always remember the technical rule: Shim coils which create magnetic fields with azimuthal symmetry different from the pulsed imaging gradients, or shim coils that create magnetic fields that have symmetry across the mid-plane different from the pulsed imaging gradients, do not experience net induced terminal voltages. All third order shims except shim coils Z2X, Z2Y and Z3 fall into this category. Selected fifth degree shims, such as Z4X, Z4Y and Z5 would likewise couple to the pulsed first order gradients.

Proof of Principle and Operability:

The following presentation is a mathematical proof of principle that the shim coil structure of the present invention will be effective in reducing the induced voltage appearing at the terminals of the shim amplifiers to lie within their intended voltage compliance limits.

SECTION A: Calculation of the Voltage Induced Across the Terminals of a Coil Exposed to a Time Dependent Field Consider an elemental dipole consisting of n turns enclosing an area dA and linked by a time dependent magnetic field, $B_\perp$, perpendicular to the plane of the loop. See FIG. 6. If the magnetic flux linked by this elemental dipole loop is $d\Phi$ and the induced voltage is dV, then $$dV = -n\frac{d\Phi}{dt} = -n\frac{dB_\perp}{dt}dA.$$

Now suppose that this elemental dipole is located at a position $(\rho,\phi,z)$ and is part of a distribution of turns constituting a coil. The distribution of turns is defined as $n(\rho,\phi,z)$ which represents a turns stream function; it is the local dipole moment per unit area per unit current. The voltage induced in this loop becomes $$dV = -n(\rho,\phi,z)\frac{dB_\perp(\rho,\phi,z)}{dt}dA$$

and the voltage induced across the terminals of the coil can be calculated by integrating this expression over the surface of the coil $$V = -\int_S n(\rho,\phi,z)\frac{dB_\perp(\rho,\phi,z)}{dt}dA.$$

Suppose that the coil in question is a shim coil and the time dependent field is due to an imaging gradient coil. If the distribution of turns in the shim coil, and the distribution of the component of the magnetic field perpendicular to the surface of the coil are both known then the voltage induced across the terminals of the coil can be calculated using this expression.

If the shim coil is wound on the surface of a disc located at an axial position, $z_0$, and extending radially from $\rho=\rho_{01}$ to $\rho=\rho_{02}$ then the perpendicular component of magnetic field is the axial field component, $B_z$, and the terminal voltage becomes $$V = -\int_{\rho=\rho_{01}}^{\rho_{02}}\int_{\phi=0}^{2\pi} n(\rho,\phi)\frac{dB_z(\rho,\phi,z_0)}{dt}\rho d\rho d\phi.$$

If the shim coil is wound on the surface of a cylinder located at a radial position, $\rho_0$, and extending axially from $z=z_{01}$ to $z=z_{02}$ then the perpendicular component of magnetic field is the radial field component, $B_\rho$, and the terminal voltage becomes $$V = -\int_{z=z_{01}}^{z_{02}}\int_{\phi=0}^{2\pi} n(z,\phi)\frac{dB_\rho(\rho_0,\phi,z)}{dt}\rho_0 dz d\phi.$$

In the above expressions, the turns distribution $n(\rho,\phi,z)$ is determined by the designer of the shim coil in such a way that the design criteria, such as constraints on field strength, field purity, electrical resistance and self inductance, etc, are satisfied. However, if also a constraint on the magnitude of the voltage induced across the terminals of the shim coil is to be included in the design criteria then during the design process the designer must be able to evaluate the expressions for coil terminal voltage given above. This requires knowledge of the field distribution, $B(\rho,\phi,z)$, due to the imaging gradients in the vicinity of the shim coil.

If the disposition of the electrical windings of the imaging gradient coil were known then the field distribution could be calculated, or more simply, the same goal could be met by applying constraints to the mutual inductance between shim coil and imaging gradient coil, in which case the field distribution would not be required. However, since the disposition of the electrical windings is usually available only to the manufacturer of the imaging gradient coil, its field distribution is unknown and the shim coil designer cannot use the above expressions in the form presented.

Nevertheless, under certain circumstances, there is a way of making an approximation to the field distribution that is adequate for achieving the same goal. In the central region of an imaging gradient coil it is necessary that the primary gradient, i.e., that gradient which is used for encoding spatial information, should be substantially free of field impurities which would result in image degradation. In practical terms this means that at any point in the region of interest the field due to all impurities should not exceed about 5% to 10% of the ideal field. Thus in the region of interest any gradient coil produces a field distribution which is closely approximated by the field distribution due to its primary gradient.

This means that in the central region of an imaging gradient coil the above expressions for shim coil terminal voltage may be modified by replacing the total fields $B_\rho$ and $B_z$ respectively by the fields $B_{\rho\ np}^{mp}$ and $B_{z\ np}^{mp}$ due to the primary gradient alone, where mp and np are respectively the order and degree of the spherical harmonic corresponding to the primary gradient produced by the imaging gradient coil. Explicitly the expressions for terminal voltage become, respectively for radially disposed coils and axially disposed coils, $$V = -\int_{\rho=\rho_{01}}^{\rho_{02}}\int_{\phi=0}^{2\pi} n(\rho, \phi) \frac{dB_{z np}^{mp}(\rho, \phi, z_0)}{dt} \rho d\rho d\phi$$

and $$V = -\int_{z=z_{01}}^{z_{02}}\int_{\phi=0}^{2\pi} n(z, \phi) \frac{dB_{\rho np}^{mp}(\rho_0, \phi, z)}{dt} \rho_0 dz d\phi.$$

The expression for the surface integral $$V = -\int_S n(\rho, \phi, z) \frac{dB_{\perp np}^{mp}(\rho, \phi, z)}{dt} dA$$

is general and can be used for designing coils wound on a surface of any shape provided that the radial, $B_{\rho\ np}^{mp}$, and axial, $B_{z\ np}^{mp}$, field components of the primary gradient produced by the imaging gradient coil are known.

Thus, inductively coupled shim coils that are intended to be members of a set of coils mounted on a shim coil insert located in the central region of imaging gradient coils can be designed by taking advantage of these expressions for calculating induced terminal voltage.

It is deemed important here to point out clearly and to emphasize properly what is the meaningful outcome of and true value for the mathematical analysis presented above. That result is: The use of the field due to the primary gradient only (which is typically known), instead of the total field (which is normally unknown), is both novel and unforeseen. In this sense, the mathematical expressions presented above are also unique in their determinations and implications. These expressions are also quite general in effect since no particular imaging gradient has been specified. Therefore, these expressions will provide the basis for many shim coil structural designs and constructions which will couple to any imaging gradient coil of any order and any degree. This constitutes the essence of the various embodiments of the present invention.

In the following sections, an example of how these mathematical expressions are used specifically for a chosen imaging gradient and shim coil geometry is given. The Example provided herein is merely one illustrative and representative instance of how to design/provide an axially disposed shim coil structure that is operational and exhibits an induced terminal voltage which is marked reduced when the shim coil structure is placed in the vicinity of an X imaging gradient coil. Such unique shim coil structures would be of the Class Z2X, Z4X, Z6X, etc.

To summarize, if these premises are valid, then this expression provides the basis for calculating the voltages induced:

(i) Across individual saddles of shim coils (ii) Across the terminals of shim coils It also provides the basis for designing/providing shim coils in which the net voltage across their terminals is zero. This is true only if the shim coils are contained within the central region of the imaging gradient coils where the total magnetic field can be characterized by the magnetic field due to that of the primary gradient of the imaging gradient coil. These conditions are met for shim coils which are part of a shim insert assembly designed to fit inside the bore of an imaging gradient coil.

Given below will be an example of the procedure that should be followed to calculate the voltage induced in an axially disposed shim coil that inductively naturally couples to a linear imaging gradient coil. In this the spherical harmonic representation of the field due to the imaging gradient coil will be used. In preparation for this the next section develops an explicit representation of spherical harmonic field components.

SECTION B: Imaging Gradient Fields Represented in Terms of Spherical Harmonics in Spherical Polar Coordinate Form The expression for the magnetic scalar potential in interior spherical harmonics is given by $$\Psi = \sum_{m=0}^{\infty}\sum_{n=m}^{\infty} \Psi_n^m(r, \theta, \phi)$$

where in spherical polar coordinates, $(r,\theta,\phi)$, $$\Psi_n^m(r,\theta,\phi) = A_n^m r^n P_n^m(u)\cos(m\phi) + B_n^m r^n P_n^m(u)\sin(m\phi).$$

In this expression $P_n^m(u)$ is an associated Legendre function of order m and degree n with argument $u=\cos(\theta)$. The terms $A_n^m$ and $B_n^m$ are source strengths. (See Appendix I: Principles of Field Correction for a more detailed explanation of the notation used in association with spherical harmonics).

Differentiation of this expression with respect to z and $\rho$ leads respectively to the axial and radial components of magnetic field $B_z$ and $B_\rho$. Thus, $$B_z = -\mu_0 \frac{d\Psi}{dz} \text{ and } B_\rho = -\mu_0 \frac{d\Psi}{d\rho}.$$

Writing $G_{n-1}^m = \mu_0 A_n^m$ we get, for the component which includes $\cos(m\phi)$, $$B_{z_{n-1}}^m = -G_{n-1}^m r^{n-1}(n+m)P_{n-1}^m(u)\cos(m\phi)$$

$$B_{\rho_{n-1}}^m = -G_{n-1}^m \frac{r^{n-1}}{2}\left[(1-\delta_m^0)(n+m)(n+m-1)P_{n-1}^{m-1}(u) - (1+\delta_m^0)P_{n-1}^{m+1}(u)\right]\cos(m\phi)$$

where $\delta_m^0$ is the Kronecker delta which has the values $\delta_0^0=1$ for m=0 and $\delta_m^0=0$ for m≠0. $G_{n-1}^m$ is the harmonic source strength in units of T/m$^{n-1}$. (The analysis for the component which includes sin(m$\phi$) is analogous to that which follows and for simplicity is omitted). Simplifying the expression for $B_\rho$ to eliminate $\delta_m^0$ leads to $$m=0 \quad B_{\rho_{n-1}}^0 = G_{n-1}^0 r^{n-1} P_{n-1}^1(u)$$

$$m\neq 0 \quad B_{\rho_{n-1}}^m = -G_{n-1}^m \frac{r^{n-1}}{2}\left[(n+m)(n+m-1)P_{n-1}^{m-1}(u) - P_{n-1}^{m+1}(u)\right]\cos(m\phi)$$

And we note that if k>l then $P_l^k(u)=0$.

In the immediately following section the field due to an X imaging gradient coil is shown in spherical harmonic form and in cylindrical coordinate form, the latter being convenient for inclusion in the formulae given above for calculating induced terminal voltage.

SECTION C: Field Due to an X Imaging Gradient Coil Represented in Terms of Spherical Harmonics in Cylindrical Polar Coordinate Form We are interested in the inductive coupling which occurs between pulsed imaging gradient coils and shim coils having the same symmetry, e.g., an X-gradient coil and a Z2X shim coil because for this situation high voltages may be induced by the X-gradient coil across the terminals of the Z2X shim coil. In particular, excessively high voltages will have an adverse effect on the operation of the shim amplifier which supplies power to the shim coil and which is connected to these terminals. At best the shim amplifier will lose control over the current being supplied to the shim coil and at worst it will be damaged. This is an important example because the Z2X shim coil is a member of the class of third-degree coils, the other members being Z3, Z2Y, ZC2, ZS2, C3 and S3, none of which couples to the X-gradient coil in such a way that a net voltage occurs across its terminals. (See Appendix I: Principles of Field Correction for an explanation of the notation used for identifying spherical harmonic components).

Significant improvement in image quality is achieved if a full set of third-degree shim coils is available. Therefore, it is important that the Z2X shim should be included; this is only practical if it can be designed in such a way that it is substantially decoupled inductively from the X imaging gradient coil.

It shall also be noted that, in the following, all arguments made concerning the interaction of an X-gradient coil and a Z2X shim coil are also directly applicable to a Y-gradient coil and a Z2Y shim coil since the symmetry relationship between such a gradient coil and its associated shim coil is identical.

The primary field produced by an X-gradient coil is the $B_{z_1}^1$ axial field component, i.e., an m=1 field with cos($\phi$) azimuthal symmetry. Accompanying this field component is a series of higher harmonic $B_{z_{n-1}}^1$ components and corresponding radial field components, $B_{\rho_{n-1}}^1$. Thus, in general an X-gradient coil will produce total fields $B_z^1$ and $B_\rho^1$ due to a set of field components where $$B_z^1 = -\sum_{n=2}^{\infty} G_{n-1}^1 r^{n-1}(n+1)P_{n-1}^1(u)\cos(\phi)$$

$$B_\rho^1 = -\sum_{n=2}^{\infty} G_{n-1}^1 \frac{r^{n-1}}{2}\left[(n+1)nP_{n-1}^0(u) - P_{n-1}^2(u)\right]\cos(m\phi)$$

In spherical polar coordinate form the first few terms in each series can be written as:

$$B_z^1 = -G_1^1 r\, 3P_1^1(u)\cos(\phi)$$
$$-G_2^1 r^2 4P_2^1(u)\cos(\phi)$$
$$-G_3^1 r^3 5P_3^1(u)\cos(\phi)$$
$$-G_4^1 r^4 6P_4^1(u)\cos(\phi)$$
$$-G_5^1 r^5 7P_5^1(u)\cos(\phi) - \ldots\ldots$$

$$B_\rho^1 = -G_1^1 r\, 3P_1^0(u)\cos(\phi)$$
$$-G_2^1 \frac{r^2}{2}\left[12P_2^0(u) - P_2^2(u)\right]\cos(\phi)$$
$$-G_3^1 \frac{r^3}{2}\left[20P_3^0(u) - P_3^2(u)\right]\cos(\phi)$$
$$-G_4^1 \frac{r^4}{2}\left[30P_4^0(u) - P_4^2(u)\right]\cos(\phi)$$
$$-G_5^1 \frac{r^5}{2}\left[42P_5^0(u) - P_5^2(u)\right]\cos(\phi) - \ldots\ldots$$

Written in cylindrical polar coordinate form the above expressions become.

$B_z^1 = -G_1^1 3\rho\, \cos(\phi)$ $-G_2^1 12z\rho\, \cos(\phi)$ $-G_3^1 30(z^2-\rho^2/4)\rho\, \cos(\phi)$ $-G_4^1 60(z^2-3\rho^2/4)z\rho\, \cos(\phi)$ $-G_5^1 105(z^4-3z^2\rho^2/2+\rho^4/8)\rho\, \cos(\phi)-$ $B_\rho^1 = -G_1^1 3z\, \cos(\phi)$ $-G_2^1 6(z^2-3\rho^2/4)\cos(\phi)$ $-G_3^1 10(z^2-9\rho^2/4)z\, \cos(\phi)$ $-G_4^1 15(z^4-9z^2\rho^2/2+5\rho^4/8)\cos(\phi)$ $-G_5^1 21(z^4-15z^2\rho^2/2+25\rho^4/8)z\, \cos(\phi)-$ In an X-gradient coil the $G_1^1$ strength, (X field harmonic), is maximized and the strength of higher degree field harmonics such as $G_2^1$,(ZX), $G_3^1$,(Z2X), $G_4^1$,(Z3X) and $G_5^1$, (Z4X), etc., are minimized so as to improve the linearity of the magnetic field due to the X-gradient coil. This is true whatever the physical configuration of the gradient coils generating the X-gradient field. (It should be noted that if the X-gradient coil is conventionally designed so that it is symmetric about the mid-plane, i.e., z=0, then harmonics in which the harmonic degree n−1 is even will have substantially zero strength anyway).

Thus, in the region of interest the total axial field distribution, $B_z^1$, is, to a good approximation, given by that due to the X field harmonic, $B_{z1}^1$, alone, i.e., $$B_z^1 \approx B_{z1}^1 = -G_1^1 3\rho \cos(\phi) = (-3G_1^1)x = G_x x$$

where the term $G_x$ is the strength of the X harmonic generated by the X-gradient coil in T/m as conventionally defined. The $G_x$ strength is known from the specifications of the imaging gradient coil. Knowing this strength we can calculate not only the axial field distribution due to that harmonic but also the radial field distribution, $B_{\rho 1}^1$, due to that harmonic from $$B_{\rho 1}^1 = -G_1^1 3z \cos(\phi) = G_x z \cos(\phi)$$

and provided that the fields associated with the $G_2^1$, (ZX) and $G_3^1$, (Z2X), etc., are small, (as they must be to create a linear X-gradient field), then in the region of interest to a good approximation we may take the total radial field component, $B_\rho^1$, to be characterized by the expression $$B_\rho^1 \approx B_{\rho 1}^1 = -G_1^1 3z \cos(\phi) = G_x z \cos(\phi)$$

The form $B_\rho^1 = G_x z \cos(\phi)$ will be used later to illustrate how the voltage induced across the terminals of a shim coil coupled to an X-gradient coil is calculated.

In the next section an example will be given of a turns stream function appropriate for designing shim coils to be mounted on cylindrical winding forms.

SECTION D: A Turns Stream Function Suitable for Shim Coils Mounted on Cylindrical Coil Forms A typical shim coil insert is formed from one or more axially disposed segments seg, each of which comprises a number of saddles distributed azimuthally. Each axially disposed segment seg has the same azimuthal distribution of turns, but each seg has a unique axial distribution.

On the surface of a cylinder there is no variation in the radial dimension and the generic three-dimensional turns stream function n(ρ,ϕ,z) contracts to the two-dimensional form n(ϕ,z). This can be conveniently represented as the product of two one-dimensional stream functions describing the variation in the azimuthal and axial directions. Thus $$n(\phi,z) = Nf(\phi)g(z)$$

where N is the total number of turns in a single saddle.

Figure 3:
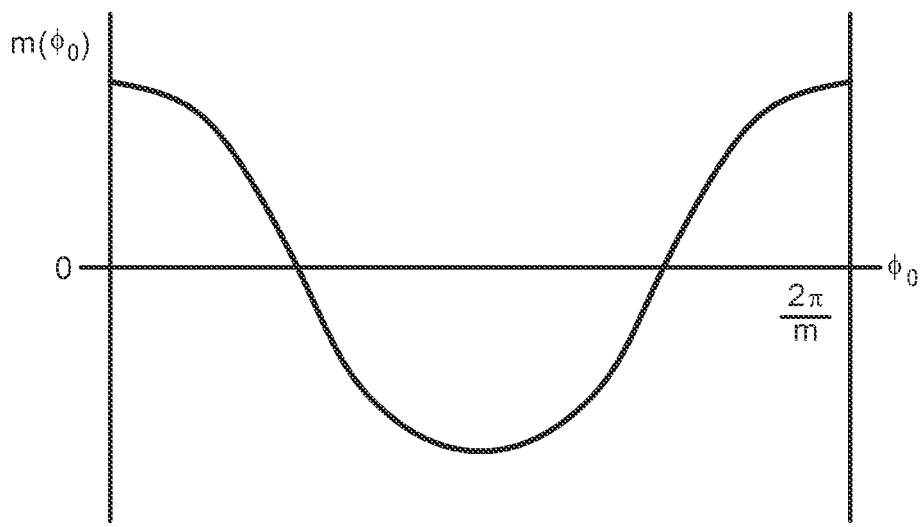
FIG. 3 is an illustration showing a distribution of turns that azimuthally is proportional to $\cos(m\varphi_0)$.

In the azimuthal direction the range required is from ϕ=0 to ϕ=2π and a suitable form for f(ϕ) is $$f(\phi) = \cos(m\phi)$$

because the azimuthal symmetry of the magnetic field created by that shim coil will be identical to that of the azimuthal distribution of current. For example a shim coil in the X family, (m=1), has two saddles in the range ϕ=0 to ϕ=2π, and a shim coil in the C3 family, (m=3), has six saddles in the range ϕ=0 to ϕ=2π. In general, there will be 2m saddles in the range ϕ=0 to ϕ=2π. See FIG. 3 which shows a distribution of turns that azimuthally is proportional to cos(mϕ₀).

Figure 1A:
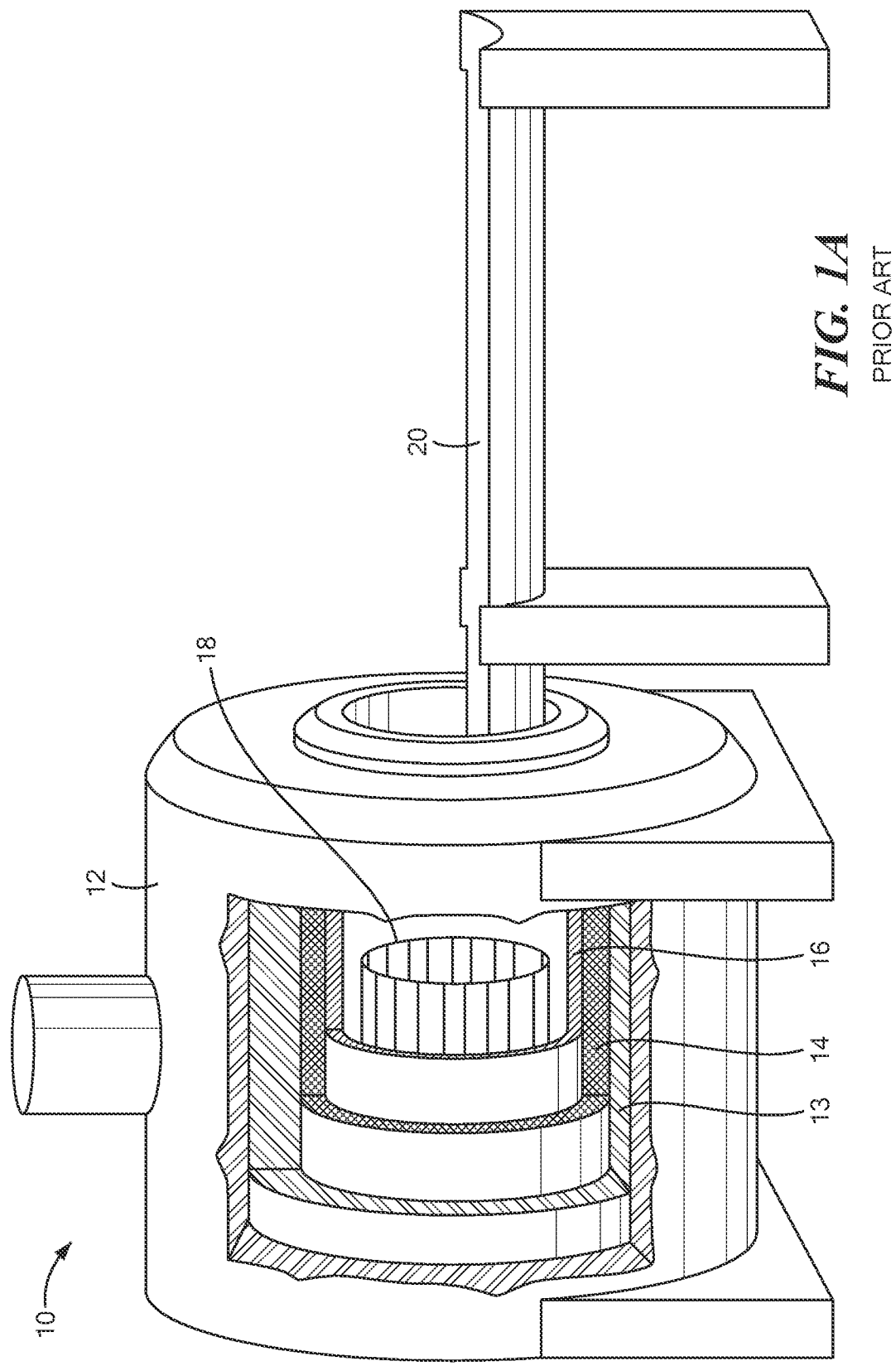
FIG. 1A illustrates the basic components of a typical superconducting magnet system.
Figure 1B:
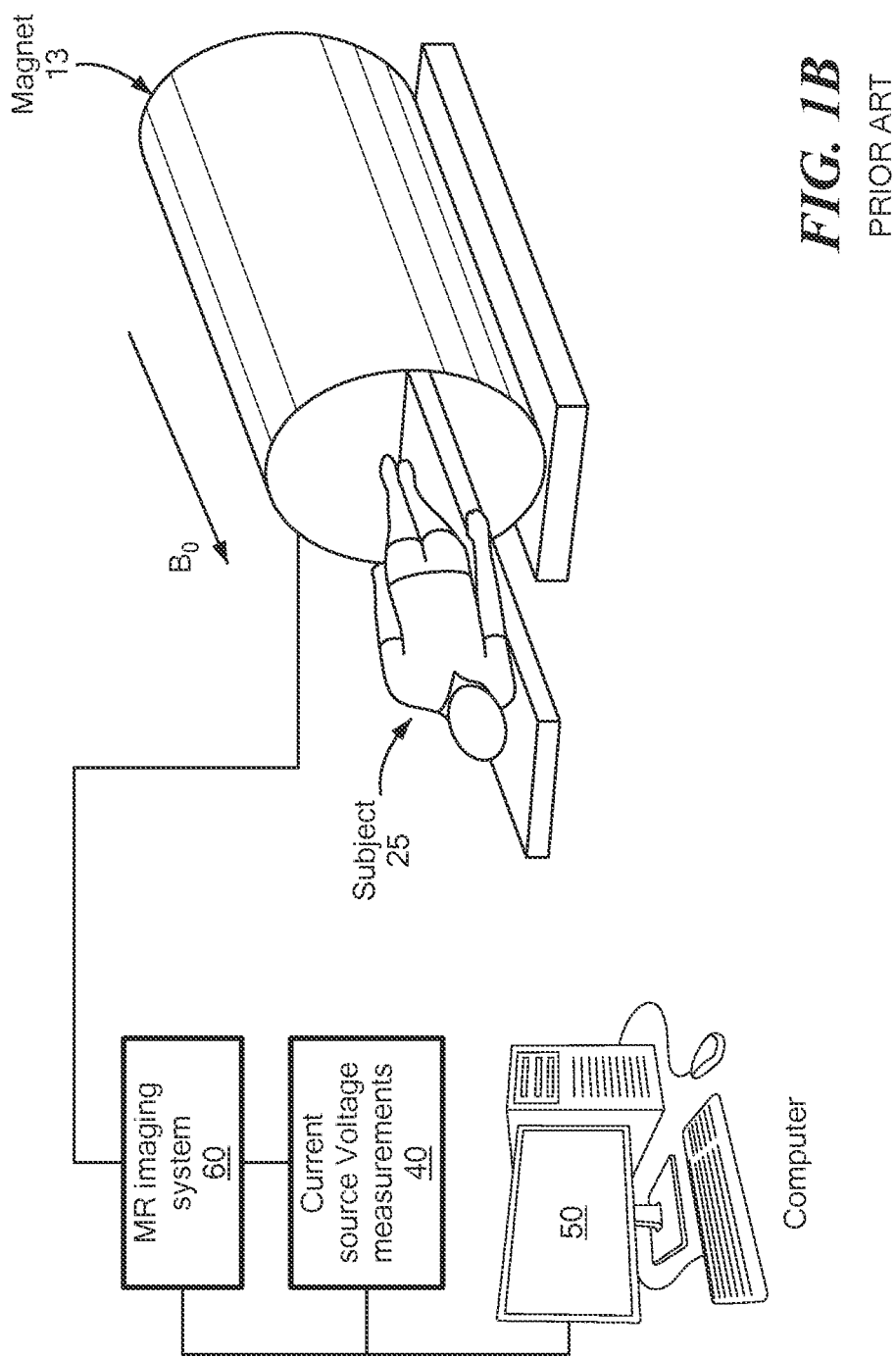
FIG. 1B illustrates some details in a traditional magnetic resonance system.
Figure 1C:
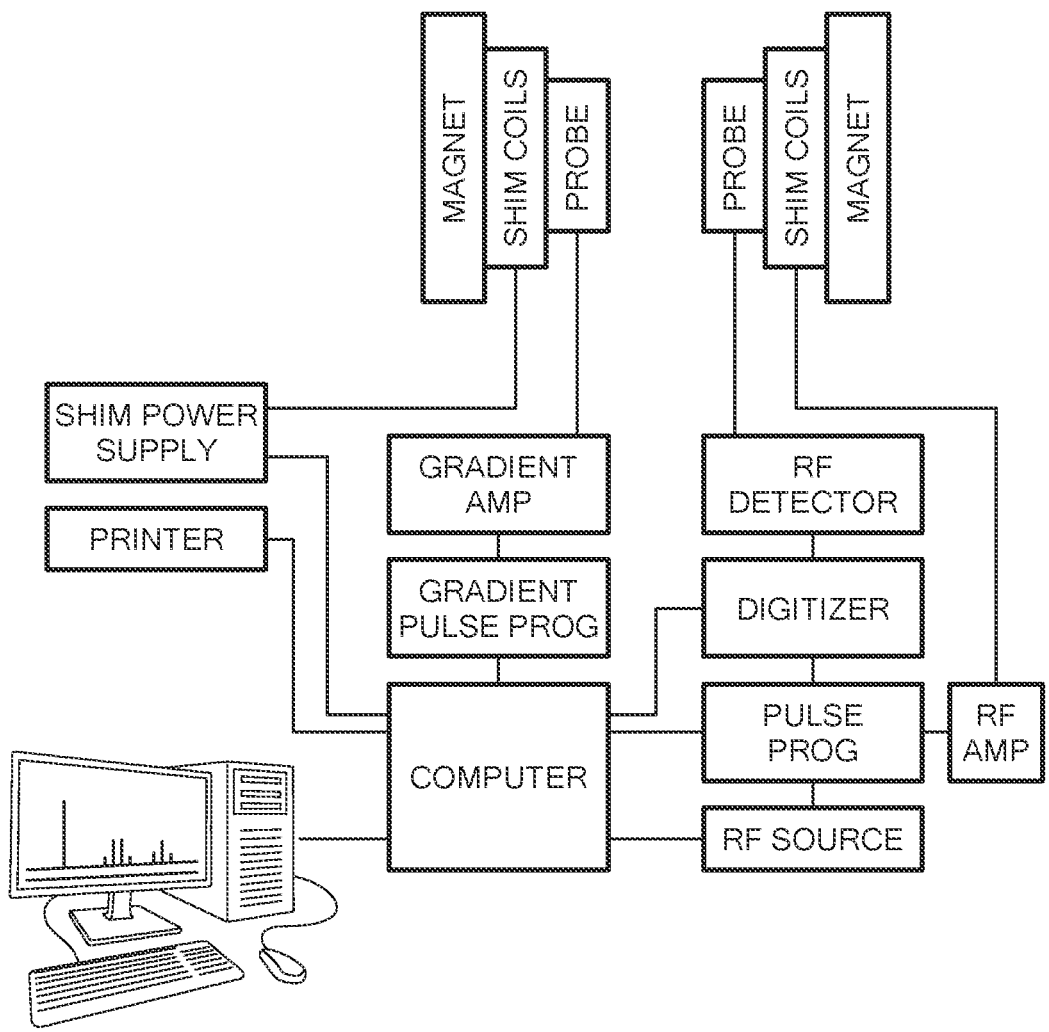
FIG. 1C illustrates other structural features of a traditional magnetic resonance system.
Figure 2:
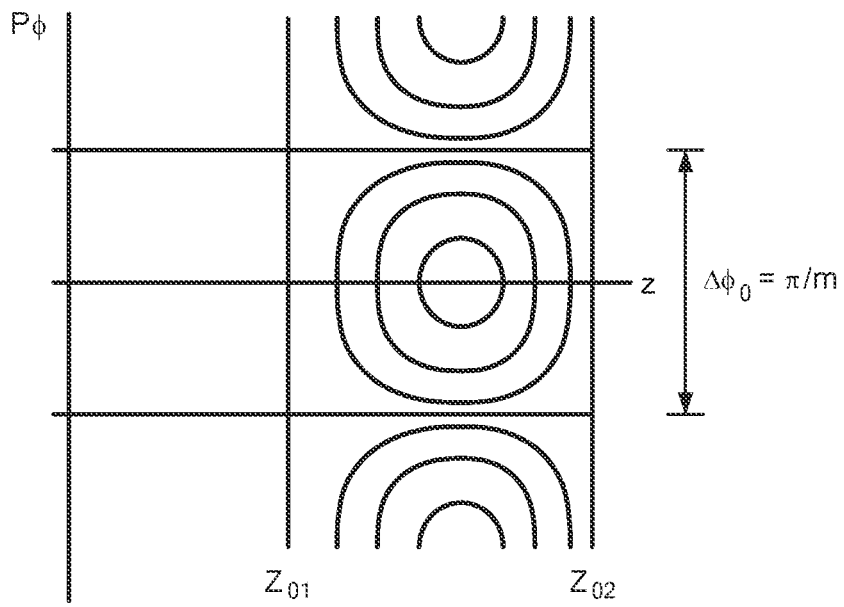
FIG. 2 is an illustration showing a segment of shim coil extending from $Z0_1$ to $Z0_2$ axially and comprising 2m saddles azimuthally between 0 and 2n.

Consider a segment seg of a shim coil extending axially from z=z₀₁ to z=z₀₂ and comprising 2m saddles disposed azimuthally between ϕ=0 to ϕ=2π. See FIG. 2 which shows a segment of shim coil extending from Z0₁ to Z0₂ axially and comprising 2m saddles azimuthally between 0 and 2Π.

When designing a shim coil, a number of performance specifications must be met. These may include, meeting the strength requirements of the primary gradient while minimizing resistive power dissipation, limiting the deviation of the total field from the desired field, minimizing the strength of certain spherical harmonic impurity fields, and of particular relevance to this invention, limiting the induced terminal voltage to less than a desired value.

Figure 4:
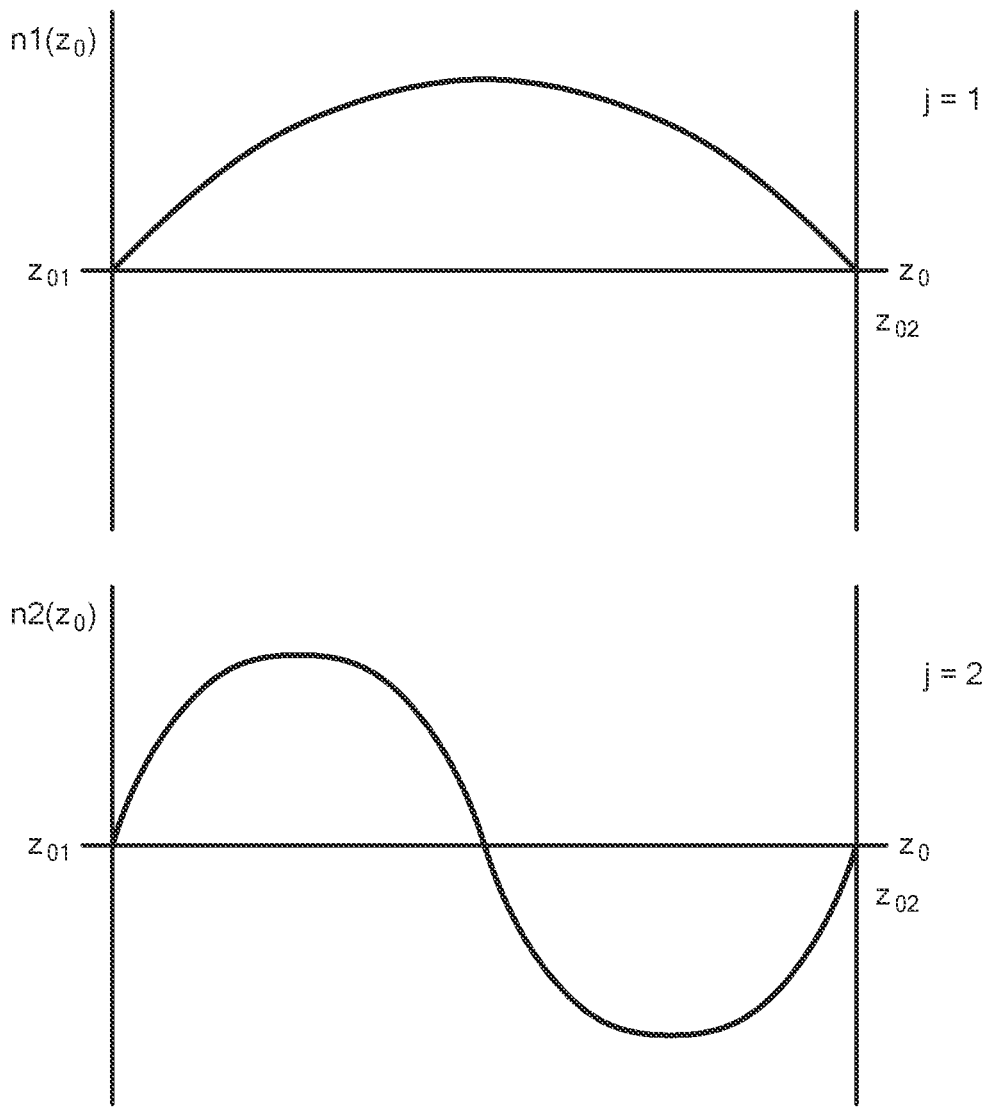
FIG. 4 is an illustration showing a distribution of turn stream function components that axially is proportional to $$\sin\left(\frac{(z-z_{01})}{(z_{02}-z_{01})}j\pi\right);$$

Because of this, it is necessary to have the ability to manipulate the shape defined by the turns stream function in the axial direction. This can be achieved by adopting a Fourier synthetic approach. Thus a suitable form for g(z) is $$g(z) = \sum_{j=1}^{j\,max} w(j) \sin\left(\frac{(z-z_{01})}{(z_{02}-z_{01})} j\pi\right)$$

where j is an integer in the range 1 to a maximum value chosen by the designer and where w(j) is a weight factor. FIG. 4 illustrates this function for the cases j=1 and j=2 and shows that the distribution of turn components axially is proportional to $$\sin\left(\frac{(z-z_{01})}{(z_{02}-z_{01})} j\pi\right);$$

Figure 5:
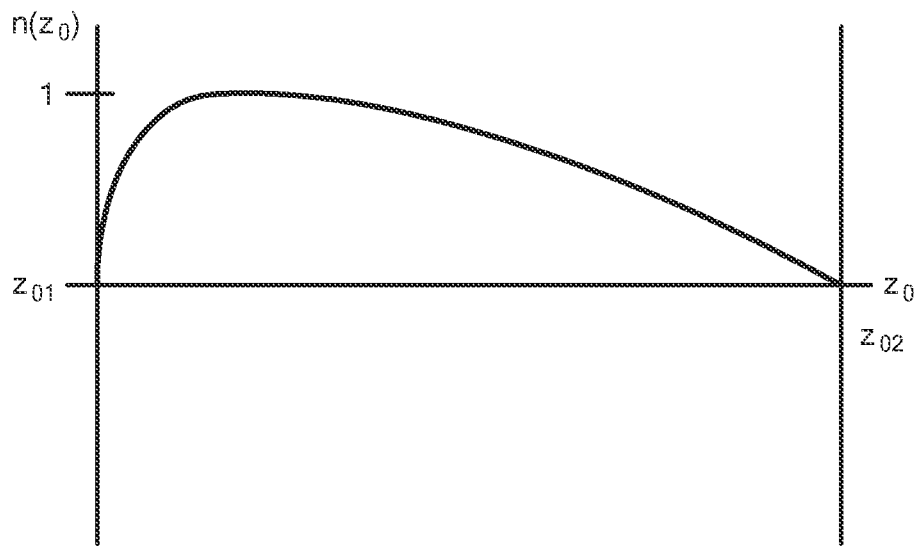
FIG. 5 is an illustration showing the sum of all turn components $$n(z_0) = \sum_{j=1}^{jmax} nj(z_0)$$

The weights are normalized in such a way that in the range z=z₀₁ to z=z₀₂ the maximum value of the function g(z) is unity. Thus $$g(z)|_{max} = \left[\sum_{j=1}^{j\,max} w(j) \sin\left(\frac{(z-z_{01})}{(z_{02}-z_{01})} j\pi\right)\right]_{max} = 1. \quad \text{See Fig. 5}$$

The number of axially disposed segments and the weight factors, w(j), associated with each one are chosen in such a way that the design specifications are met. An exemplary method for doing this will be presented in a later section. The result of combining the explicit expressions for the azimuthal and axial components for the turns stream function is $$n(\phi, z) = N \sum_{j=1}^{j\,max} w(j) \sin\left(\frac{(z-z_{01})}{(z_{02}-z_{01})} j\pi\right) \cos(m\phi).$$

If multiplied by the current in each turn, the above expression constitutes the current stream function, so we can regard the function n(ϕ,z) as the current stream function per unit current. The current stream function is also the dipole moment per unit area so the function n(ϕ,z) can be regarded as the dipole moment per unit area per unit current at the position (ϕ,z)

To meet all design criteria it may be necessary for the shim coil to comprise more than one axially disposed shim coil segment. Each one of those segments will have unique values for z₀₁, z₀₂, N and the set w(j), j=1, j max.

For the exemplary case of the terminal voltage induced in a shim coil with symmetry the same as that of the X-gradient, which has m=1 azimuthal symmetry, the turns stream function becomes $$n(\phi, z) = N \sum_{j=1}^{j\,max} w(j) \sin\left(\frac{(z-z_{01})}{(z_{02}-z_{01})} j\pi\right) \cos(\phi)$$

In the next section this expression together with the field distribution for a X-gradient coil will be incorporated into the general expression for the induced voltage across a single axially disposed shim coil segment to obtain an explicit formula for the induced voltage in terms of shim coil design parameters and X-gradient coil operational parameters. The shim coil segment is located at a radius $\rho_0$ and extends axially from $z=z_{01}$ to $z=z_{02}$. See FIG. 7 which shows a radial field penetrating element of a saddle coil wound on the surface of a cylinder.

SECTION E: Voltage Induced Across the Terminals of a Susceptible Shim Coil Due to the Field of an X-Gradient Coil From SECTION A above, the general expression for the voltage induced across the terminals of one axially disposed shim coil segment located in the central region of an imaging gradient whose primary gradient is of order mp and degree np is given by $$V = -\int_{z=z_{01}}^{z_{02}} \int_{\phi=0}^{2\pi} n(z,\phi) \frac{dB_{\rho np}^{mp}(\rho_0, \phi, z)}{dt} \rho_0 dz d\phi$$

This equation is the general expression for the induced voltage and could be solved using the time dependent radial field components associated with pulsed coils of any azimuthal symmetry.

For example, if there were a non-linear pulsed imaging gradient such as a pulsed C2 coil then the voltage induced in a Z2C2 shim coil would be of interest. However, for the time being, we will concentrate on the immediately practically important situation where the interaction is between a pulsed X-gradient coil and any shim that also has $\cos(\phi)$ symmetry.

For an X-gradient coil mp=1 and np=1, and this expression becomes $$V = -\int_{z=z_{01}}^{z_{02}} \int_{\phi=0}^{2\pi} n(z,\phi) \frac{dB_{\rho 1}^{1}(\rho_0, \phi, z)}{dt} \rho_0 dz d\phi$$

where $B_{\rho 1}^{1}$ is the field due to the primary harmonic of the X-gradient coil. From SECTION C the field due to the X-gradient in the central region as represented by its primary harmonic is given by $$B_\rho^1 = G_x z \cos(\phi)$$

From SECTION D, the turns stream function for a susceptible shim coil such as the Z2X shim is given by $$n(\phi, z) = N \sum_{j=1}^{jmax} w(j) \sin\left(\frac{(z-z_{01})}{(z_{02}-z_{01})} j\pi\right) \cos(\phi)$$

Substituting the expression for the field due to the X-gradient coil and the expression for the shim coil turns stream function into the expression for the induced voltage leads to $$V = -N\rho_0 \frac{dG_x}{dt} \sum_{j=1}^{jmax} v(j)$$

where v(j) is a function associated with the $j^{th}$ stream function component defined by the following expression.

$$v(j) = w(j) \int_{z=z_{01}}^{z_{02}} \int_{\phi=0}^{2\pi} \sin\left(\frac{(z-z_{01})}{(z_{02}-z_{01})} j\pi\right) \cos(\phi)^2 d\phi dz$$

The result of integrating in $\phi$ is:

$$I(\phi) = \int_{\phi_0=0}^{2\pi} \cos(\phi)^2 d\phi = \pi$$

The integral in z is:

$$I(z) = \int_{z=z_{01}}^{z_{02}} z \sin\left(\frac{(z-z_{01})}{(z_{02}-z_{01})} j\pi\right) dz$$

Integration by parts results in:

$$I(z) = (-)\frac{(z_{02}-z_{01})}{j\pi}\left((-)^j z_{02} - z_{01}\right)$$

Substituting $I(\phi)$ and $I(z)$ into the expression for v(j) above gives:

$$v(j) = -w(j)\frac{(z_{02}-z_{01})}{j}\left((-)^j z_{02} - z_{01}\right)$$

Therefore the voltage induced across the terminals of the $i^{th}$ segment of an axially disposed shim coil is given by $$V(i) = \frac{dG_x}{dt} N(i)\rho_0(i)(z_{02}(i) - z_{01}(i)) \sum_{j=1}^{jmax} \frac{w(i,j)}{j}\left((-)^j z_{02}(i) - z_{01}(i)\right)$$

If the shim coil consists of nseg segments then the voltage induced across the terminals of that shim coil is given by $$V = \frac{dG_x}{dt} \sum_{i=1}^{nseg} N(i)\rho_0(i)(z_{02}(i) - z_{01}(i)) \sum_{j=1}^{jmax} \frac{w(i,j)}{j}\left((-)^j z_{02}(i) - z_{01}(i)\right)$$

The rate of change of gradient strength with respect to time can be calculated from the gradient strength and gradient rise time associated with a particular imaging sequence.

Thus, provided that the primary source of radial field is due to the x harmonic component of the X-gradient coil, the above formula will allow the voltage across the terminals of any shim coil to be calculated. If necessary, with elementary modifications of the above analysis, it is possible to derive a formula which will allow the voltage across individual saddles within a shim coil to be calculated.

Furthermore, since there is now an analytical expression for calculating the induced voltage, this expression can be used for applying a constraint that will force the terminal voltage across a shim coil to lie within prescribed limits. This constraint is satisfied by selecting appropriate coil radial and axial positions ($\rho_0(i), z_{01}(i)$) and ($\rho_0(i), z_{02}(i)$) for each of the nseg segments comprising the system, and for each segment selecting an appropriate set of magnitudes and signs for the stream function weights w(i, j) for j=1 to j=j max, the value of j max being at the discretion of the shim coil designer. The set of individual segments comprising a shim coil resulting from this procedure will include segments with opposite terminal voltage polarity such that the total terminal voltage across the shim coil is limited to a desired value.

A method for accomplishing this is described in detail by the next part of the disclosure. This method is operative and allows multiple constraints to be applied simultaneously, while at the same time an expensive resource is minimized.

III. An Optimization Method Suitable for Applying Constraints That Will Result in the Satisfaction of Design Specifications In practice, constraints may be applied using well documented constrained optimization procedures that are available from the literature. (See Pierre[1] for a comprehensive treatment concerning methods for maximizing or minimizing functions). An exemplary method is described below; it is that which was used for obtaining the exemplary design for the Z2X shim in the presence of an X-gradient described by Section IV below.

A method of unconstrained minimization will be described first. Then a method of modifying it in such a way that constraints can be applied will be described.

1. The conjugate direction method due to Powell, (see Press[2] below), is an unconstrained minimization method. It is particularly effective in minimizing a function of several independent variables. Such a function, commonly referred to as the objective function, is a performance measure. The principle of Powell's method, which is iterative, is as follows.

At the beginning of an iteration there is a starting point defined by an initial set of values of N independent variables together with the value of the performance measure, i.e., objective function, associated with those variables. Starting from the initial point, a line minimization is carried out in the direction of the first independent variable, i.e., with all other independent variables held constant, the value of Variable 1 is changed until a minimum of the performance measure is found. Taking this point as a new starting point a line minimization is carried out in the direction of the second independent variable. This process is repeated N times, i.e., N line minimizations are performed. At this point the initial direction, i.e. that of Variable 1, is discarded and a new direction is added, that direction being the direction that connects the point at the beginning of the iteration to that at the end of the iteration. This constitutes one iteration of the basic procedure. This basic procedure is repeated N times. If the objective function is of quadratic form then this cycle will find its minimum.

Objective functions encountered in practice are not so well behaved and so the procedure given above will not in general result in a minimum. Therefore, the value of the performance measure, i.e., objective function, at the end of the cycle is compared with the value of the performance measure at the beginning. If these values are equal then the performance measure, i.e., objective function, has been minimized; the values of the independent variables existing at the end of that cycle are those which minimize the objective function. If the value of the objective function at the end of that cycle is less than that at its beginning, then the value of the objective function is still decreasing and it has not been minimized.

In this instance, another cycle of N iterations of the basic procedure is performed, i.e., the cycle is repeated using an initial point defined by the values of the independent variables at the end of the previous cycle but with a new set of directions. Press describes methods for calculating this new direction set. That is the essence of the method but it is more complex than that described above. Space does not permit a detailed account to be given here; for a comprehensive treatment the reader is directed to Reference 2 given below.

In this exemplary case, the independent variables would be the coil positions ($\rho_0(i), z_{01}(i)$) and ($\rho_0(i), z_{02}(i)$) and the values of the weights w(i, j), associated with the turns stream function all for the nseg segments comprising the shim coil. An initial set of independent variables is required to start the first iteration in Powell's method as described above. The values of the variables selected for inclusion in this initial set may be based on the results of a previous design, or if this is not available then reasonable guesses, based on the experience of a coil designer, may be used.

The strength of a field gradient generated by shim a coil is limited by the ability to dissipate the heat which is produced in its windings. Hence, management of resistive heating is an extremely important factor in designing a shim coil. Consequently, an appropriate performance measure, i.e., objective function, would be the resistive power dissipation, RPOWER. The power dissipation is a function of the independent variables so we can write, RPOWER($\rho_0, z_{01}, z_{02}, w(i, j)$).

When designing a shim coil, in addition to minimizing the performance measure exemplified by the resistive power dissipation, it is necessary to meet certain design specifications. In other words it is necessary to restrict the values of certain dependent variables such as the magnitude of a magnetic field harmonic gradient that would degrade the quality of the magnetic field or, of particular relevance in this document, the magnitude of the voltage induced across the terminals of a shim coil. This means that inequality constraints must be imposed. If the maximum allowable value of the gradient due to an undesirable field harmonic is G max and the maximum allowable value of the voltage across the terminals of the shim coil is V max then in mathematical terms the associated inequality constraints would be respectively, $G \leq G$ max and $V \leq V$ max.

2. As noted above, Powell's method is one of unconstrained minimization, resulting in the minimization of an unconstrained performance measure. Therefore, in its simplest form it will not allow the application of inequality constraints involving, for example, limitations on magnetic field inhomogeneity or induced shim coil terminal voltage. However, there is a simple way to adapt the method so that constraints can be applied. This involves the concept of penalty functions. See Reference 1 below.

A penalty function is a function which is added to the performance measure and which detracts from good performance, as measured by the performance measure, when an associated constraint is violated. Particularly useful penalty functions, p, for inequality constraints, as exemplified respectively by the inequality constraints on impurity gradient strength and terminal voltage, are $p_G = 0$ for $G \leq G$ max and $p_G = (G - G \text{ max})^2$ for $G > G$ max, i.e., when the constraint is being violated, $p_V = 0$ for $V \leq V$ max and $p_V = (V - V \text{ max})^2$ for $V > V$ max, i.e., when the constraint is being violated.

Note that here, one defines the term 'penalized performance measure' or $P_p$ as the unconstrained performance measure augmented by the sum of all associated penalty functions, each of which is weighted by a coefficient e.g., $c_G$ and $c_V$. The penalized performance measure is otherwise known as the modified objective function. Thus, for the example being used $$P_p = \text{RPOWER} + c_G p_G + c_V p_V.$$

Powell's method is now applied to the penalized performance measure, and the minimization algorithm finds values of the independent variables $(\rho_0(i), z_{01}(i))$, $(\rho_0(i), z_{02}(i))$ and $w(i, j)$ that result, first in the inequality constraints being satisfied, i.e., $G \leq G$ max and $V \leq V$ max, and subsequently the performance measure RPOWER being minimized. Thus the final result is a set of independent variables $(\rho_0(i), z_{01}(i))$ $(\rho_0(i), z_{02}(i))$ and $w(i, j)$ where the resistive power is minimized subject to the inequality constraints being satisfied.

3. The augmented Lagrangian multiplier method due to Bertsekas[3] is a better way to create a penalty function. In this, illustrating the method now with just the induced voltage inequality constraint, instead of the form $p_V = 0$ for $V \leq V$ max and $p_V = c_V(V - V \text{ max})^2$, for $V > V$ max.

The penalty function is of the form $p_V = 0$ for $V \leq V$ max and $p_V = \mu_V(V - V \text{ max}) + c_V(V - V \text{ max})_2$ for $V > V$ max.

So explicitly, the penalized performance measure would be $P_p = \text{RPOWER} + \mu_V(V - V \text{ max}) + c_V(V - V \text{ max})^2$ for $V > V$ max.

Initial values are given to the parameters $\mu$, (the Lagrangian multiplier), and c, (the penalty parameter). Appropriate initial values are determined by numerical experimentation; it has been found that $\mu = 0$, and c in the range 1 to $10^6$ are reasonable starting values. Choosing too high a value for c can lead to situations where numerical ill-conditioning is encountered. Choosing c too low can lead to a large number of cycles before convergence is achieved. After each cycle of Powell's method, which results in minimization of the penalized performance measure, Bertsekas's algorithm assesses progress towards minimization and appropriately modifies the values of $\mu$ and c in preparation for the next cycle.

After a number of cycles, the combination of Powell's and Bertsekas's methods selects a set of independent variables that, in the exemplary case, satisfies the inequality constraint, i.e., $V \leq V$ max so that in subsequent cycles the value of the penalty term, $p_V$, is set at zero and the unconstrained performance measure is minimized. Ultimately, the constraint, i.e., $V \leq V$ max, is satisfied while at the same time the unconstrained performance measure, i.e., the resistive power dissipation, RPOWER$(\rho_0, z_{01}, z_{02}, w(i, j))$, is minimized.

The strength of the primary gradient and the purity of the magnetic field generated by the shim are also issues so the magnitudes of a number of spherical harmonics must also be controlled. This can be done in a manner analogous to that described above for controlling the magnitude of the voltage induced across the terminals of the shim coil. As many constraints as are necessary can be applied in parallel during the optimization procedure.

[1] Optimization Theory with Applications, Donald A. Pierre, Dover Publications, 1986, which is hereby incorporated by reference herein in its entirety.

[2] Numerical Recipes, Chapter 10 Minimization or Maximization of Functions, W. H. Press, B. P. Flannery, S. A. Teukolsky, W. T. Vetterling, Cambridge University Press, 1986, which is hereby incorporated by reference herein in its entirety.

[3] Constrained Optimization and Lagrange Multiplier Methods, D. P. Bertsekas, Academic Press, 1982 which is hereby incorporated by reference herein in its entirety.

IV. An Illustrative Example of Minimally Coupled Z2X Shim Coil Designed Using the Novel Formula for Calculating Terminal Voltage A Z2X shim coil that is minimally coupled to the X imaging gradient coil was designed using the principles and methods described above. In particular, the induced terminal voltage was calculated using the assumption that the total field due to the X-gradient coil could be well approximated by that of the field corresponding to its primary gradient.

FIG. 8 shows a 180 degree azimuthal span of the resulting winding pattern. It can be seen that there are four azimuthally disposed segments distributed asymmetrically with respect to the mid-plane. The segments extend axially from −300 mm to 175 mm and their mean radius is about 220 mm. The current sense in the coil whose turn boundaries are depicted with broken lines is opposite to that in the coils whose turn boundaries are depicted with solid lines. Coils are numbered 1 to 4 starting with the coil whose edge is at −300 mm. For an imaging X-gradient coil whose gradient is changing at a rate of 200 T/m/s the voltages predicted to be induced in coil segments 1 to 4 are respectively, −49.1 V, 19.4 V, −0.7 V and 30.3 V resulting in a net terminal voltage of 0.1 V.

The asymmetry of the winding pattern about the mid-plane that is evident in this design results from restrictions on the maximum axial extent of the windings on one side of the shim coil. This shim coil is one component of a set of shim coils to be mounted on an insert that can be retrofitted into the central region of a whole body imaging system. The purpose of the insert is to improve the quality of images of the human brain; and therefore it must be short enough at one end that it does not extend beyond the shoulders—i.e., the distance from the centre of the imaging volume to the shoulders determines the maximum length of the shim coil insert. If this dimensional constraint had not been in place then a more efficient symmetrical design would have resulted.

Because, of necessity, the design was asymmetrical about the mid-plane, in order to maintain field purity it was necessary to control the strength not only of the X, Z4X, etc., field harmonics—but also to the ZX, Z3X, etc., field harmonics.

V. The Constrained Optimization Method of the Present Invention

The Scope and Definition of the Method:

Based upon all the principles and points of information given above, a previously unknown and unavailable design optimization method directed to providing exact specifications for the fabrication of improved shim coils result. Accordingly, the unique design method can be defined in the following terms.

A constrained optimization method for designing an improved shim coil that substantially reduces the inductive coupling occurring in an MR assembly between the pulsed imaging gradient coils and an in-bore positioned shim coil having the same symmetry as the gradient coils, wherein the pulsed imaging gradient coils are permanently arranged around the periphery of the bore of an MRI magnet in an MRI assembly, typically X, Y and Z, and the improved shim coil is suitable for positioning inside the central volume of the bore cavity space of an MRI magnet, said method for constrained optimization design of a shim coil comprising the steps of:

Step 1: Generating a shim coil design suitable for fabrication which has at least one axial segment wherein each axial segment comprises a number of saddles distributed azimuthally;

Step 2: Using the expression $$V = -\int_S n(\rho, \phi, z) \frac{dB_{\perp np}^{mp}(\rho, \phi, z)}{dt} dA$$

to calculate the magnitude of the voltage (V) induced across the terminals of the shim coil design, wherein $n(\rho,\phi,z)$ is the turns stream function and $B_{\perp np}^{mp}(\rho,\phi,z)$ is the component of the field due to only the primary harmonic generated by the imaging gradient that is perpendicular to the surface of said shim coil; and then Step 3: Constraining the magnitude of the induced voltage across the terminals of the shim coil design to be within a prescribed range of acceptable voltages. Illustratively, this may be done by selecting appropriate coil radial and axial positions $(\rho_0(i),z_{01}(i))$ and $(\rho_0(i),z_{02}(i))$ for each of the nseg segments comprising the system, and for each segment selecting an appropriate set of magnitudes and signs for the stream function weights $w(i, j)$ for $j=1$ to $j=j$ max.

In addition, the present invention also provides a method for fabricating an improved shim coil which may be defined by the following.

A fabrication method for making an improved shim coil structure that substantially reduces the inductive coupling occurring in an MR assembly between the pulsed imaging gradient coils and an in-bore positioned shim coil having the same symmetry as the gradient coils, wherein the pulsed imaging gradient coils are permanently arranged around the periphery of the bore of an MRI magnet in an MRI assembly, typically X, Y and Z, and the improved shim coil is suitable for positioning inside the central volume of the bore cavity space of an MRI magnet, said fabrication method comprising the steps of:

Step 1: Designing a shim coil to be constructed as a structure which has at least one axial segment wherein each axial segment comprises a number of saddles distributed azimuthally;

Step 2: Using the expression $$V = -\int_S n(\rho, \phi, z) \frac{dB_{\perp np}^{mp}(\rho, \phi, z)}{dt} dA$$

to calculate the magnitude of the voltage (V) induced across the terminals of said designed shim coil, wherein $n(\rho,\phi,z)$ is the turns stream function and $B_{\perp np}^{mp}(\rho,\phi,z)$ is the component of the field due to only the primary harmonic generated by the imaging gradient that is perpendicular to the surface of said designed shim coil;

Step 3: Constraining the magnitude of the induced voltage across the terminals of said designed shim coil to be within a prescribed range of acceptable voltages; then Step 4: Determining the requisite specifications for manufacturing said designed shim coil having a constrained induced voltage as fixed values for the coordinates for the positions of the axial segments $(\rho_0(i),z_{01}(i))$ and $(\rho_0(i),z_{02}(i))$, and the weight factors $w(j)$ for $j=1$ to $j=j$ max, and
the numbers of turns in each segment $N(i)$; and Step 5: Constructing a shim coil whose manufactured structure is in accordance with said determined specifications.

1. Please note that the general formula $$V = -\int_S n(\rho, \phi, z) \frac{dB_{\perp np}^{mp}(\rho, \phi, z)}{dt} dA$$

is specifically for a linear X gradient coil and the specific turns stream function for shim coils wound on cylinders. It does not cover the cases of Z gradient coils or non-linear gradient coils of any kind; or other plausible turns stream functions.

This is shown by Section A where the expression for the surface integral $$V = -\int_S n(\rho, \phi, z) \frac{dB_{\perp np}^{mp}(\rho, \phi, z)}{dt} dA$$

is general and can be used for designing coils wound on a surface of any shape provided that the radial, $B_{\rho np}^{mp}$, and axial, $B_{z\ np}^{mp}$, field components of the primary gradient produced by the imaging gradient coil are known.

2. It will be noted and appreciated also that the design specifications are formulated in terms of a number of constraints on parameters relevant to the performance of the shim coil being designed. For example, as has been explained in Section III above, the expression V≤V max is a constraint; it means that there is a design specification such that the voltage, V, induced across the terminals of the shim coil should be less than a certain maximum voltage, Vmax. Therefore, meeting design specifications is equivalent to satisfying a number of constraints. The way that a design specification is met—i.e., a constraint is satisfied, is explained in Section III.

The Scope and Definition of the Article of Manufacture:

The present invention also provides an unique and markedly improved shim coil insert as a discrete article of manufacture. Accordingly, the improved shim coil article is defined in the alternative as follows.

A first definitional statement is:

An MR assembly including a series of X, Y and Z pulsed imaging gradient coils permanently arranged around the periphery of the bore of an MRI magnet in an MR assembly and a portable shim coil insert suitable for in-bore positioning inside the cavity space of the MRI magnet, the improvement of a shim coil demonstrating a substantially reduced inductive coupling with the pulsed imaging gradient coils, said improved shim coil comprising:

a design shim coil having the capability of providing a supplementary magnetic field gradient on-demand sufficient to substantially cancel a high degree inhomogeneity of the primary magnetic (B0) field present within the cavity space of the MRI magnet in the MR assembly;

a set of nseg axially disposed segments, wherein each axial segment comprises a number of saddles distributed azimuthally;

a coil symmetry similar to that of the X, Y and Z pulsed imaging gradient coils permanently arranged around the periphery of the bore of an MRI magnet;

the use of the expression $$V = \frac{dG_x}{dt} \sum_{i=1}^{nseg} N(i)\rho_0(i)(z_{02}(i) - z_{01}(i)) \sum_{j=1}^{jmax} \frac{w(i,j)}{j}((-)^j z_{02}(i) - z_{01}(i))$$

to calculate the total induced voltage across the set of nseg segments comprising the shim coil; and the effect of a constraint upon that total calculated induced voltage that will markedly reduce the magnitude of the induced voltage across the terminals of the shim coil to lie within a prescribed range of acceptable voltages.

The alternative second definitional statement is:

An improved shim coil article comprising:

a designed shim coil having the capability of providing a supplementary magnetic field gradient on-demand sufficient to substantially cancel a high degree inhomogeneity of the primary magnetic (B0) field present within the cavity space of the MRI magnet in the MR assembly;

a set of nseg axially disposed segments, wherein each axial segment comprises a number of saddles distributed azimuthally;

a coil symmetry similar to that of the X, Y and Z pulsed imaging gradient coils permanently arranged around the periphery of the bore of an MRI magnet;

the use of the expression $$V = \frac{dG_x}{dt} \sum_{i=1}^{nseg} N(i)\rho_0(i)(z_{02}(i) - z_{01}(i)) \sum_{j=1}^{jmax} \frac{w(i,j)}{j}((-)^j z_{02}(i) - z_{01}(i))$$

to calculate the total induced voltage across the set of nseg segments comprising the shim coil;

the effect of a constraint upon that total calculated induced voltage that will markedly reduce the magnitude of the induced voltage across the terminals of the shim coil to lie within a prescribed range of acceptable voltages; and a set of specifications for said designed shim coil having a constrained induced voltage which has fixed values for the coordinates for the positions of the axial segments ($\rho_0(i), z_{01}(i)$) and ($\rho_0(i), z_{02}(i)$), and the weight factors w(j) for j=1 to j=j max, and
the numbers of turns in each segment N(i).

1. It will be noted and appreciated that the expression $$V = \frac{dG_x}{dt} \sum_{i=1}^{nseg} N(i)\rho_0(i)(z_{02}(i) - z_{01}(i)) \sum_{j=1}^{jmax} \frac{w(i,j)}{j}((-)^j z_{02}(i) - z_{01}(i))$$

appears throughout the language of both the method and the article of manufacture. It is emphasized and repeatedly pointed out that this formula applies exclusively to the specific case of shim coils wound on the surfaces of cylinders influenced by X, (or Y), gradient coils. It was derived in Section II as an illustrative example of the general formula $$V = -\int_S n(\rho, \phi, z) \frac{dB^{mp}_{inp}(\rho, \phi, z)}{dt} dA$$

in connection with the illustrative example of the design of a Z2X shim coil.

Consequently it does not apply to shim coils, (e.g., Z3), wound on the surfaces of cylinders under the influence of Z gradient coils. There is a formula analogous to that shown above which is relevant to the case of shim coils wound on the surfaces of cylinders under the influence of Z gradient coils; this formula is also available.

The Prescribed Range of Acceptable Voltages:

It is deemed desirable to identify herein what is a prescribed range of acceptable voltages having a markedly reduced magnitude of induced voltage which is caused by the effect of a constraint upon that total calculated induced voltage across the terminals of the shim coil.

As is commonly recognized in the industry, an induced voltage of 500 volts or greater is not acceptable; yet there must be some value of induced voltage across the terminals of the constructed shim coil. Accordingly, the broadest possible range is a constrained voltage greater than zero and less than 500 volts.

Within the broadest available range of prescribed values, a more generally useful—but not optimal—range of prescribed values would be a constrained voltage value greater than zero but less than about 100 volts.

A subset range of preferred prescribed voltage values would be represented by constrained voltages ranging from about 25 volts to about 75 volts.

Lastly, a most preferred and optimal constrained voltage value would be about 50 volts.

VI. The Structural Parts of the Shim Coil Insert

Structures Having Conventional Shim Coil Formats:

Structurally, shim coils are traditionally formatted as a series of individual wire windings, or two dimensional conductive patterns formed on a cylindrical surface—e.g., by etching a copper sheet; and the conductor forming each shim coil is typically arranged in such a manner as to manifest, by means of electric current, a specific correcting function selected from a "basis set" of field terms that represent the spherical harmonic solution to Laplace's equation. A detailed description of such field terms and the principles of field correction is presented by Appendix I hereinafter.

As is well established, the central equation governing the magnetic field distribution within a spatial volume through which no electric current passes is the Laplace equation $\nabla^2 \Psi = 0$, in which $\Psi$ is the scalar magnetic potential.

The Laplace equation is most conveniently solved using the spherical polar coordinate system. This framework also provides a calculated "basis set" of field terms by which to express those inhomogeneities existing along the Z axis of the imaging volume of the magnet; and therefore these field terms are a mathematical expression of the nature of the distortions over the $B_z$ vector, the only relevant component of the $B_0$ field as regards homogeneity.

The "basis set" of field terms will also yield and recite the potential corrections by which to neutralize and cancel the inhomogeneities existing in the main magnetic field; and recites a set of correcting field functions (expressed in spatial positional coordinates) which can be manifested and exerted using an active shimming approach.

The basis set of terms recites the correcting field terms as a series of Cartesian coordinate positions which must be electrically corrected in order to solve the spherical harmonic distortions that are commonly encountered in magnetic resonance spectroscopy. It is noted that the basis set of correcting field functions is effective for and provides mathematical solutions for all orders, (m), and all degrees, n (where n≥m) of harmonic distortions that might exist within the $B_0$ magnetic field.

However, in actual practice, only some active shim coils having wire windings for those few correcting field terms allocated to cancelling a spherical harmonic distortion of the $1^{st}$ and $2^{nd}$ degree are conventionally made or used. It is particularly noted that little or no attention at all is given to using shimming to cancel a spherical harmonic distortion of the higher orders and degrees—i.e., harmonic distortions of the $4^{th}$, $5^{th}$, and $6^{th}$ degrees.

Thus even today, very few magnetic resonance assemblies provide shim coils which are able to overcome and correct magnetic field inhomogeneities beyond $2^{nd}$ degree harmonic distortions. Even among the notable exceptions to this practice, there are only a handful of research-designed magnetic resonance assemblies (mostly ultra high field magnetic resonance scanners) which are capable of correcting some, but not all, $3^{rd}$ degree harmonic distortions.

It is noted also that spherical harmonic shims that are embodiments of the present invention can be created by: Specifically designed circuits arranged so as to create substantially pure spherical harmonic terms; or by use of coils that generate a set of shim terms of the same order but different degrees. A linear combination of fields generated by a combination of coils with independent current sources can result in an arbitrarily pure combination of field terms within the same order. This combination of coils and use technique is frequently called a 'MATRIX shim'. However, there are also a range of non-harmonic shim designs and use techniques that are not subject to this application.

A Highly Preferred Shim Coil Insert Structure

A greatly preferred format for the present invention is the portable in-bore shim coil structure and article of manufactured described in full by U.S. Pat. No. 8,536,870 to Punchard et al., entitled "Shim Insert for High-field MRI Magnets", and granted on Sep. 17, 2013, the text and figures of which are expressly incorporated by reference herein. The disclosed shim coil insert is able to produce higher degree shimming effects on-demand (i.e., the correction of at least one high degree inhomogeneity) over the $B_z$ vector component of the main magnetic ($B_0$) field; and is suitable for use with those magnetic resonance assemblies and systems operating at 3T to 12T magnetic field strengths.

The preferred structure of the shim coil insert in U.S. Pat. No. 8,536,870 comprises a movable at will cylinder-like chamber which can be tangibly sited at any desired location within the bore volume of an MRI magnet in a magnetic resonance assembly; is a hollow housing formed solely of non-magnetic materials; has an encompassing perimeter wall with corresponding discrete exterior and interior wall surfaces; and has at least one open end for entry and egress. The chamber also has fixed length and girth dimensions; and a demarcated internal shimming space serving as a limited examination zone which is not only bounded by the perimeter walls, but also is sized and preferably contoured to accept and hold a targeted ROI in a chosen subject.

The portable shim coil insert also provides at least one array of surface coils able to carry electric current and which are collectively disposed in azimuthal symmetry and axial distribution upon the supporting wall surface of the encompassing perimeter wall; and are operative on-demand to produce multiple supplemental magnetic gradients sufficient to cancel a range of inhomogeneities in the main magnetic ($B_0$) magnetic field then present within the limited examination zone of the demarcated internal shimming space. The array of surface coils which are collectively disposed in azimuthal symmetry and axial distribution in this insert structure markedly improves the quality of in-vivo spectroscopy and/or imaging of any desired ROI in a subject or object then positioned within the limited examination zone of the demarcated internal shimming space in the insert.

Accordingly, the full breadth and scope of the present invention provides a prepared in advance in-bore shim coil insert which is portable and movable at will to any desired location within the bore volume of a conventionally manufactured NMR magnet. Note however, that the in-bore shim coil insert is typically designed to be located in the center of the gradient field (i.e., the center of the DSV) in order to achieve optimal results; and this feature should be taken into account by the operator when selecting the particular mounting location within the bore volume of the MRI magnet.

After a particular location has been selected and the shim coil insert has been mounted and secured at that site, the array of surface coils—which are collectively disposed in azimuthal symmetry and axial distribution—will be aligned and orientated to generate multiple supplemental magnetic gradients of specified size and shape (in accordance with specific field terms) of the $B_z$ component of the magnetic field everywhere within the targeted ROI; and these generated supplemental magnetic gradients will be superimposed at specified spherical polar coordinate positions over the $B_z$ vector of the main magnetic $B_0$ field then present within the physical confines of the demarcated internal shimming space of the insert; and, in this manner, will neutralize and cancel at least some high order, high degree inhomogeneities for any desired ROI in a subject or object then placed within the limited examination zone of the construction.

The capability of the shim coil insert to create such higher order, higher degree corrections of magnetic field inhomogeneities within the physical confines of its demarcated internal shimming space, will in turn, substantially improve both the quality and certainty of obtained empirical results for at least three different clinical/diagnostic procedures—i.e, magnetic resonance imaging ('MRI'), nuclear magnetic resonance spectroscopy ('MRS'), and nuclear magnetic resonance spectroscopic imaging ('MRSI').

VII. Advantages and Benefits of the Improved Shim Coil Structure

A diverse range of unexpected advantages and major benefits are provided by the present invention. Notable among these are the following:

1. The shim coil insert of the present invention can be located in either of two different formats and settings:
   (i) A first format and setting employs an improved shim coil insert which is structured as a series of individual wire windings, or two dimensional conductive patterns, formed on a cylindrical surface which is permanently located adjacent to the three pulsed gradient coils (the X-gradient coil, the Y-gradient coil, and the Z-gradient coil) encompassing the bore of an NMR magnet in a MR assembly. This is the conventional placement and traditional format which encompasses and surrounds the bore volume of the NMR magnet is well established in the technical field and is illustrated herein by Prior Art Figs A, B, and C respectively.
   (ii) A second and far preferred format and setting is the portable shim coil insert described in full by U.S. Pat.

No. 8,536,870. In this preferred setting, the improved shim coil insert is a portable article which is initially positioned at one location and then may be subsequently re-positioned at will anywhere within the bore volume of the NMR magnet, at any time and for any reason. However, one presumes that the improved shim coil insert structure will be typically located in the center of the primary magnetic field (gradient null), and that the anatomy of interest will be placed in the center of that volume. Great caution is recommended in this respect because moving the improved shim coil insert in the FOV of the gradient may cause coupling effects that are very undesirable for safety reasons.

Once secured in a chosen position, the improved shim coil insert remains stationary; and the targeted ROI is moved into, and then out of the immobilized demarcated internal volume of the insert. Then, if and when desired, the one construct, without making any substantive changes to its component parts or manner of assembly, can be moved as a single entity to another chosen site as needed or desired, so long as the subsequently chosen site lies within the bore cavity of the MRI magnet (given the safety precautions stated above).

The advantage of this structural format is that the improved shim coil insert is both portable and re-locatable on-demand; may be moved at any time and for any reason after being secured and used at an initial site; and can be re-positioned serially on multiple occasions at many different use locations within the totality of the bore volume of the MRI magnet.

2. Not only can $3^{rd}$ degree inhomogeneities be corrected and cancelled by the improved shim coil insert; but also $4^{th}$, $5^{th}$ and $6^{th}$ degree inhomogeneities can be corrected and cancelled, if and when desired. Consequently if one wished or were required by use circumstances to do so, a range of multiple $3^{rd}$ to $6^{th}$ degree inhomogeneities can be concurrently corrected in-situ using the present invention. In fact, the correction practice may be extended in principle to include corrections of arbitrarily high order and degree, and is limited only by certain practical issues such as power consumption and spatial resolution of conductor placement.

3. The improved shim coil insert may be constructed as a discrete article of manufacture suitable for operation in alternative use circumstances, which are: (i) As a retro-fitted addition and later introduced appendage to be located within the bore volume of a NMR magnet in a presently existing magnetic resonance system; and alternatively (ii) as an original equipment manufacture ("OEM") article which is employed as a requisite and operational component in a newly built or erected magnetic resonance assembly.

4. The structured shim coil will also demonstrate at least one performance specification selected from the group consisting meeting the strength requirements of the primary gradient while minimizing resistive power dissipation, limiting the deviation of the total field from the desired field, and minimizing the strength of specific spherical harmonic impurity fields.

The embodiments of the invention described above are intended to be merely exemplary; numerous variations and modifications will be apparent to those skilled in the art. All such variations and modifications are intended to be within the scope of the present invention.

APPENDIX I: PRINCIPLES OF FIELD CORRECTION

A. In a region that is free of magnetic sources, the magnetic scalar potential, $\Psi$, satisfies Laplace's equation, $\nabla^2\Psi=0$. Differentiation of a solution of this equation with respect to the axial coordinate, z, results in a solution for the axial component of magnetic field, Bz, which is the component of magnetic field that is relevant to magnetic resonance imaging and to nuclear magnetic resonance applications. In an interior region, i.e., a region that is closer to the origin than any source of the magnetic field, in spherical polar coordinates, this solution is $$Bz(r, \theta, \phi) = \sum_{m=0}^{\infty}\sum_{n=m}^{\infty}(A_{n+1}^m r^n(n+m+1)P_n^m(u)\cos(m\phi) + B_{n+1}^m r^n(n+m+1)P_n^m(u)\sin(m\phi))$$

where Bz is the magnetic flux density (loosely referred to as the magnetic field strength) at a field point r, $\theta$, $\varphi$ and where r is the polar radius, $\theta$ is the polar angle, and $\varphi$ is the azimuthal angle. [See any advanced text on electricity and magnetism, e.g., Smythe, (Static and Dynamic Electricity, McGraw-Hill, 1968) or Stratton, (Electromagnetic Theory, McGraw-Hill, 1941), each of which is hereby incorporated herein by reference in its entirety].

The solution for this interior field is valid inside a sphere whose surface does not intersect any coil corner. It constitutes a double infinite series of components each of which is the product of a source term, $A_{n+1}^m$ or $B_{n+1}^m$, in units of $T/m^n$, and respectively a field term $r^n P_n^m(u)\cos(m\phi)$ or $r^n P_n^m(u)\sin(m\phi)$ in units of $m^n$ which is a function of the coordinates of the field point. Each source term characterizes the strength of the component, i.e., the gradient strength and each field term characterizes the way in which this strength is spatially distributed. The function $P_n^m(u)$ is an associated Legendre function with argument, u, equal to the cosine of the polar angle, $\theta$. The magnetic field components described above are known as spherical harmonics and constitute a set of orthogonal functions.

When describing certain characteristics of a particular spherical harmonic or a shim coil that is associated with a spherical harmonic, one needs to make use of the terms degree and order. Unfortunately, these terms are used inconsistently and interchangeably in the literature. Therefore, since there is evidently no universally accepted standard for these notations, this text explicitly adopts the notation of such widely used and accepted authorities as Gradsteyn and Ryzhik, (Tables of Integrals and Products, Academic Press, 1980); Abramowitz and Stegun, (Handbook of Mathematical Functions, Dover Publications, 1970); Hobson, (The Theory of Spherical and Ellipsoidal Harmonics, (Cambridge University Press, 1931); and The NIST Digital Library of Mathematical Functions, (http://dlmf.nist.gov/ Chapter 14), each of which is hereby incorporated herein by reference in its entirety whereby the number n is called the degree and the number m is called the order of the function $P_n^m(u)$.

Accordingly, the term degree, n, which is associated with the polar radius r, characterizes the rate at which the strength of the magnetic field changes with respect to distance from the origin along a polar radius and the term order, m, which is associated with the azimuthal angle $\varphi$, characterizes the periodicity of the strength of magnetic field in the azimuthal direction. This text refers to all harmonics which have a common order, m, as belonging to the same azimuthal symmetry family (or for brevity, just 'family'). Each individual azimuthal symmetry family comprises an infinite number of spherical harmonic members, each of which has a different degree, n. Within a given family, the lowest degree, n, is numerically equal to the order, m, of that family.

B. Any interior magnetic field can be decomposed into such a set of spherical harmonics and it is this property that is exploited for purposes of field correction. A field mapping and field decomposition procedure results in determining the strengths of a selected number of spherical harmonic field components whose presence degrades the quality of the magnetic field; the field would be of better quality, i.e., more homogeneous, if these components were not present.

The method used to improve the quality of the field involves applying a correction individually to each one of these selected components. For each spherical harmonic field component that is to be corrected, a supplementary field which has the same spatial distribution is applied. The strength of this supplementary field is equal in magnitude, but is opposite in sign, to that of the field to be corrected. The superposition of these two fields then results in cancellation of the unwanted field error.

Because the supplementary field has the same spatial distribution as the spherical harmonic field to be eliminated, this cancellation occurs everywhere. This supplementary field is provided by shim coils. For each spherical harmonic error field component that is to be corrected, there must be a corresponding shim coil that can generate a field having a spatial distribution that is substantially the same as that of the field to be corrected. The strength of the field generated by each shim coil is adjusted by changing the current in that shim coil.

It should be noted that the distinction between the part of the expression for Bz shown above which is regarded as the source term and that which is regarded as the field term is somewhat arbitrary. It is largely a matter of what a particular analyst regards as convenient and there is no scientific or industry standard. As long as the product of the source term and the field term results in the correct value for the field any convention is valid.

Consequently, although differences in usage will be encountered in the literature, the functional relation between the individual coordinates of corresponding field terms will always be the same, but the values of the field terms may differ by constant factors. A manufacturer of devices for generating and measuring magnetic field will have its own particular convention which may or may not be consistent with that of other manufacturers; to understand the magnitude of gradient strength as defined by a particular manufacturer it is necessary to know how the associated field term is defined. The system described herein, and which will be used consistently throughout this document, is substantially that currently used by Resonance Research Inc.

C. In some respects, it is easier to visualize the spatial distribution associated with each one of the spherical harmonic field components if the coordinate system is converted from spherical polar coordinate form to the equivalent rectangular Cartesian coordinate form. For this reason, it is the Cartesian coordinate form that is commonly used in the literature associated with magnetic field correction.

The conversion of coordinates is accomplished in the following way. For brevity only the cos(m$\phi$) component will be treated; the treatment of the sin(m$\phi$) component is analogous. Starting with the spherical polar coordinate form, we have $$Bz_n^m(r,\theta,\phi) = A_{n+1}^m r^n (n+m+1) P_n^m(u)\cos(m\phi).$$

The field term $r^n P_n^m(u)\cos(m\phi)$ written thus in spherical polar coordinates can be converted to a polynomial expression in cylindrical coordinates using a relation given by Smythe, (op. cit.), $$r^n P_n^m(u) = (n+m)! \sum_{k=m}^{kmax} \frac{(-)^{(k-m)/2} z^{(n-k)} \rho^k}{(n-k)!(k+m)!!(k-m)!!},$$

where k max=n or n−1, k+m is even and k jumps by two in successive terms of the summation. This results in $$Bz_n^m(\rho,\phi,z) = A_{n+1}^m (n+m+1)! \sum_{k=m}^{kmax} \frac{(-)^{(k-m)/2} z^{(n-k)} \rho^k}{(n-k)!(k+m)!!(k-m)!!}\cos(m\phi).$$

Customarily, but not universally, an additional factor which makes the highest power of z in the polynomial expression equal to unity is included. To accomplish this, the expression above is modified in the following way $$Bz_n^m(\rho,\phi,z) =$$

$$\frac{A_{n+1}^m(n+m+1)!}{(n-m)!(2m)!!}(n-m)!(2m)!! \sum_{k=m}^{kmax} \frac{(-)^{(k-m)/2} z^{(n-k)} \rho^k}{(n-k)!(k+m)!!(k-m)!!}\cos(m\phi).$$

The source term in units of $T/m^n$ is now redefined as $$G_n^m = \frac{A_{n+1}^m(n+m+1)!}{(n-m)!(2m)!!}$$

leaving the field term in units of $m^n$ as $$F_n^m(\rho,\phi,z) = (n-m)!(2m)!! \sum_{k=m}^{kmax} \frac{(-)^{(k-m)/2} z^{(n-k)} \rho^k}{(n-k)!(k+m)!!(k-m)!!}\cos(m\phi)$$

and the field is then calculated from $$B_n^m(\rho,\phi,z) = G_n^m F_n^m(\rho,\phi,z).$$

It should be noted that some authorities define the associated Legendre function as $$P_n^m(u) = (-)^m (1-u^2)^{1/2} \frac{d^m P_n^0(u)}{du^m}$$

whereas other authorities omit the $(-)^m$ factor. For reasons concerning this definition an additional factor $(-)^m$ may appear in the field term as it is encountered in the literature.

Finally, to convert from cylindrical coordinate form to Cartesian coordinate form the cosine of the multiple angle is expressed in terms of a polynomial in powers of cosines of the angle using a relation given by Gradsteyn and Ryzhik, (op. cit.), $$\cos(m\phi) = \cos^m(\phi) - \binom{m}{2}\cos^{m-2}(\phi)\sin^2(\phi) + \binom{m}{4}\cos^{m-4}(\phi)\sin^4(\phi) - \ldots$$

where the binomial coefficient $$\binom{m}{j} = \frac{m!}{j!(m-j)!}.$$

Substitution of this expression into the field term above results in such terms as $$\rho^k \cos(m\phi) = \rho^{k-m}\left(x^m - \binom{m}{2}x^{m-2}y^2 + \binom{m}{4}x^{m-4}y^4 - \ldots\right)$$

Thus the Cartesian form of the spherical harmonic field terms can be tediously derived.

It will be noted that the terms in the polynomial representing $F_n^m(\rho,\phi,z)$ given above have alternating signs. Furthermore, as the degree, n, of the Legendre term increases, the magnitudes of the individual terms within the polynomial become larger than the sum of all terms and cancellation between successive terms causes all accuracy to be lost. Thus, although the variation of field may be more easily envisaged in Cartesian coordinates, the Cartesian coordinate form of the field terms should not be used for performing numerical calculations.

The spherical harmonic form of the field terms should be used for any calculation involving fields and simple and stable recursion formulae can be used to calculate the value of the associated Legendre function $P_n^m(u)$; see W. H. Press, et al., Chapter 6 Special Functions, Numerical Recipes—The Art of Scientific Computing, First Edition, 1986. The calculation of any field term is then reduced to the product of three simple terms, i.e., the power of a number, an associated Legendre function and a circular function.

D. As the degree of the field term increases, the number of terms in the polynomial constituting the Cartesian coordinate representation of a spherical harmonic also increases and it becomes cumbersome to write it out in full when the need to refer to it arises. Consequently, to avoid such inconvenience, abbreviations are used. There are many conventions in use, but typically all involve, in one form or another, a representation of the highest power of z in the polynomial and a representation of the azimuthal symmetry.

Table 1 shows one such system. This system is very similar to that used by Resonance Research Inc. and is the system that will be used consistently hereinafter throughout this text. Table 1 shows the field terms corresponding to the first seven degrees, n=0 to n=6, of the infinite set of spherical harmonics. Within each degree are listed harmonics of order m=0 to m=n. Harmonics of order m=0 which have no azimuthal dependence are referred to as zonal or axial harmonics, and harmonics of order greater than zero are referred to as tesseral or radial harmonics. Harmonics for which m=n are sometimes referred to as sectoral harmonics.

For each harmonic, the spherical polar form, the Cartesian form and the abbreviated form are shown. It will be seen that the Cartesian form of the harmonic becomes increasingly complex as the degree increases and if the Cartesian form of the harmonics is to be used, it becomes clear that an abbreviated notation is necessary. It can be seen that in the abbreviated form the highest power of the z coordinate appears together with an indication of the family to which the harmonic belongs.

Thus, it is clear that the abbreviated form Z2C4 indicates a harmonic belonging to the family with fourfold azimuthal symmetry in which the highest power of the axial coordinate is 2. The degree of the harmonic is indicated by the sum of the power of z and the order, m. Thus the Z2C4 harmonic is of degree n=6, meaning that its strength increases as the sixth power of the polar radius.

The harmonics that are listed in Table 1 below extend beyond the range of those harmonics for which shim coils are routinely built. However, the shim coil insert on which the Z3, Z2X and Z2Y minimally coupled shims are to be mounted will include the $5^{th}$ order shims, (i.e., m equal to 5), C5 ($r^5P_5^5(u)\cos(5\phi)$), S5 ($r^5P_5^5(u)\sin(5\phi)$) and ZC5 ($r^6P_6^5(u)\cos(5\phi)$), ZS5 ($r^6P_6^5(u)\sin(5\phi)$). C5 and S5 are of $5^{th}$ degree, (n equal to 5). ZC5 and ZS5 are of $6^{th}$ degree, (n equal to 6).

TABLE 1

Field Terms in Spherical Polar Form, Cartesian Form and Abbreviated Form

| Degree n | Order m | Spherical | Cartesian $\rho^2 = x^2 + y^2$ | Abbreviation |
|---|---|---|---|---|
| 0 | 0 | $r^0P_0^0(u)$ | 1 | Z0 |
| 1 | 0 | $r^1P_1^0(u)$ | z | Z1 |
|   | 1 | $r^1P_1^1(u)\cos(\phi)$ | x | X |
|   |   | $r^1P_1^1(u)\sin(\phi)$ | y | Y |
| 2 | 0 | $r^2P_2^0(u)$ | $z^2 - (1/2)\rho^2$ | Z2 |
|   | 1 | $r^2P_2^1(u)\cos(\phi)$ | zx | ZX |
|   |   | $r^2P_2^1(u)\sin(\phi)$ | zy | ZY |
|   | 2 | $r^2P_2^2(u)\cos(2\phi)$ | $x^2 - y^2$ | C2 |
|   |   | $r^2P_2^2(u)\sin(2\phi)$ | 2xy | S2 |
| 3 | 0 | $r^3P_3^0(u)$ | $z(z^2 - (3/2)\rho^2)$ | Z3 |
|   | 1 | $r^3P_3^1(u)\cos(\phi)$ | $x(z^2 - (1/4)\rho^2)$ | Z2X |
|   |   | $r^3P_3^1(u)\sin(\phi)$ | $y(z^2 - (1/4)\rho^2)$ | Z2Y |
|   | 2 | $r^3P_3^2(u)\cos(2\phi)$ | $z(x^2 - y^2)$ | ZC2 |
|   |   | $r^3P_3^2(u)\sin(2\phi)$ | 2zxy | ZS2 |
|   | 3 | $r^3P_3^3(u)\cos(3\phi)$ | $x(x^2 - 3y^2)$ | C3 |
|   |   | $r^3P_3^3(u)\sin(3\phi)$ | $y(3x^2 - y^2)$ | S3 |
| 4 | 0 | $r^4P_4^0(u)$ | $z^4 - 3z^2\rho^2 + (3/8)\rho^4$ | Z4 |
|   | 1 | $r^4P_4^1(u)\cos(\phi)$ | $zx(z^2 - (3/4)\rho^2)$ | Z3X |
|   |   | $r^4P_4^1(u)\sin(\phi)$ | $zy(z^2 - (3/4)\rho^2)$ | Z3Y |
|   | 2 | $r^4P_4^2(u)\cos(2\phi)$ | $(x^2 - y^2)(z^2 - (1/6)\rho^2)$ | Z2C2 |
|   |   | $r^4P_4^2(u)\sin(2\phi)$ | $2xy(z^2 - (1/6)\rho^2)$ | Z2S2 |
|   | 3 | $r^4P_4^3(u)\cos(3\phi)$ | $zx(x^2 - 3y^2)$ | ZC3 |
|   |   | $r^4P_4^3(u)\sin(3\phi)$ | $zy(3x^2 - y^2)$ | ZS3 |
|   | 4 | $r^4P_4^4(u)\cos(4\phi)$ | $x^4 - 6x^2y^2 + y^4$ | C4 |
|   |   | $r^4P_4^4(u)\sin(4\phi)$ | $4xy(x^2 - y^2)$ | S4 |

TABLE 1-continued

Field Terms in Spherical Polar Form, Cartesian Form and Abbreviated Form

| Degree n | Order m | Spherical | Cartesian $\rho^2 = x^2 + y^2$ | Abbreviation |
|---|---|---|---|---|
| 5 | 0 | $r^5 P_5^0(u)$ | $z(z^4 - 5z^2\rho^2 + (15/8)\rho^4)$ | Z5 |
|   | 1 | $r^5 P_5^1(u)\cos(\phi)$ | $x(z^4 - (3/2)z^2\rho^2 + (1/8)\rho^4)$ | Z4X |
|   |   | $r^5 P_5^1(u)\sin(\phi)$ | $y(z^4 - (3/2)z^2\rho^2 + (1/8)\rho^4)$ | Z4Y |
|   | 2 | $r^5 P_5^2(u)\cos(2\phi)$ | $z(x^2 - y^2)(z^2 - (1/2)\rho^2)$ | Z3C2 |
|   |   | $r^5 P_5^2(u)\sin(2\phi)$ | $2zxy(z^2 - (1/2)\rho^2)$ | Z3S2 |
|   | 3 | $r^5 P_5^3(u)\cos(3\phi)$ | $x(x^2 - 3y^2)(z^2 - (1/8)\rho^2)$ | Z2C3 |
|   |   | $r^5 P_5^3(u)\sin(3\phi)$ | $y(3x^2 - y^2)(z^2 - (1/8)\rho^2)$ | Z2S3 |
|   | 4 | $r^5 P_5^4(u)\cos(4\phi)$ | $z(x^4 - 6x^2y^2 + y^4)$ | ZC4 |
|   |   | $r^5 P_5^4(u)\sin(4\phi)$ | $4zxy(x^2 - y^2)$ | ZS4 |
|   | 5 | $r^5 P_5^5(u)\cos(5\phi)$ | $x(x^4 - 10x^2y^2 + 5y^4)$ | C5 |
|   |   | $r^5 P_5^5(u)\sin(5\phi)$ | $y(y^4 - 10x^2y^2 + 5x^4)$ | S5 |
| 6 | 0 | $r^6 P_6^0(u)$ | $z^6 - (15/2)z^4\rho^2 + (45/8)z^2\rho^4 - (5/16)\rho^6$ | Z6 |
|   | 1 | $r^6 P_6^1(u)\cos(\phi)$ | $zx(z^4 - (5/2)z^2\rho^2 + (5/8)\rho^4)$ | Z5X |
|   |   | $r^6 P_6^1(u)\sin(\phi)$ | $zy(z^4 - (5/2)z^2\rho^2 + (5/8)\rho^4)$ | Z5Y |
|   | 2 | $r^6 P_6^2(u)\cos(2\phi)$ | $(x^2 - y^2)(z^4 - z^2\rho^2 - (1/16)\rho^4)$ | Z4C2 |
|   |   | $r^6 P_6^2(u)\sin(2\phi)$ | $2xy(z^4 - z^2\rho^2 - (1/16)\rho^4)$ | Z4S2 |
|   | 3 | $r^6 P_6^3(u)\cos(3\phi)$ | $zx(x^2 - 3y^2)z^2 - (3/8)\rho^2)$ | Z3C3 |
|   |   | $r^6 P_6^3(u)\sin(3\phi)$ | $zy(3x^2 - y^2)(z^2 - (3/8)\rho^2)$ | Z3S3 |
|   | 4 | $r^6 P_6^4(u)\cos(4\phi)$ | $(x^4 - 6x^2y^2 + y^4)(z^2 - (1/10)\rho^2)$ | Z2C4 |
|   |   | $r^6 P_6^4(u)\sin(4\phi)$ | $4xy(x^2 - y^2)(z^2 - (1/10)\rho^2)$ | Z2S4 |
|   | 5 | $r^6 P_6^5(u)\cos(5\phi)$ | $zx(x^4 - 10x^2y^2 + 5y^4)$ | ZC5 |
|   |   | $r^6 P_6^5(u)\sin(5\phi)$ | $zy(y^4 - 10x^2y^2 + 5x^4)$ | ZS5 |
|   | 6 | $r^6 P_6^6(u)\cos(6\phi)$ | $(x^2 - y^2)(x^4 - 14x^2y^2 + y^4)$ | C6 |
|   |   | $r^6 P_6^6(u)\sin(6\phi)$ | $2xy(x^2 - 3y^2)(3x^2 - y^2)$ | S6 |

We claim:

1. A fabrication method for making an improved shim coil structure that reduces an inductive coupling occurring in an MRI assembly between pulsed imaging gradient coils and a shim coil having a same symmetry as the pulsed imaging gradient coils, wherein the pulsed imaging gradient coils are permanently arranged around a periphery of a bore of an MRI magnet in the MRI assembly, and the improved shim coil structure is suitable for positioning inside a central volume of the bore of the MRI magnet, said fabrication method comprising the steps of:

designing the improved shim coil to be constructed as a structure which has at least one axial segment wherein each axial segment comprises a number of saddles distributed azimuthally;

using an expression $$V = -\int_S n(\rho, \phi, z) \frac{dB_{\perp np}^{mp}(\rho, \phi, z)}{dt} dA$$

to calculate a magnitude of a voltage (V) induced across terminals of said improved shim coil, wherein $n(\rho,\phi,z)$ is the turns stream function and $B_{\perp np}^{mp}(\rho,\phi,z)$ is a component of a field due to only a primary harmonic generated by the pulsed imaging gradient that is perpendicular to a surface of said improved shim coil;

constraining the magnitude of the induced voltage across the terminals of said improved shim coil to be within a prescribed range of acceptable voltages;

determining requisite specifications for manufacturing said improved shim coil having the constrained magnitude of the induced voltage as fixed values for:

coordinates for positions of the axial segments $\rho_0(i), z_{01}(i)$ and $\rho_0(i), z_{02}(i)$, stream weight factors $w(j)$ for $j=1$ to $j=j$ max, and number of turns in each segment $N(i)$; and constructing the improved shim coil whose manufactured structure is in accordance with said determined requisite specifications.

2. The method recited by claim 1 wherein said prescribed range of acceptable voltages is greater than zero volts and less than 500 volts.

3. The method recited by claim 1 wherein said prescribed range of acceptable voltages is greater than zero volts and less than 100 volts.

4. The method recited by claim 1 wherein said prescribed range of acceptable voltages is from 25 volts to 75 volts.

5. The method recited by claim 1 further comprising an application without any knowledge of the configuration of electrical windings of the imaging gradient coil that is inducing that voltage.

6. A constrained optimization method for designing an improved shim coil that reduces an inductive coupling occurring in an MRI assembly between pulsed imaging gradient coils and shim coil having a same symmetry as the pulsed imaging gradient coils, wherein the pulsed imaging gradient coils are permanently arranged around a periphery of a bore of an MRI magnet in the MRI assembly, and the improved shim coil is suitable for positioning inside a central volume of the bore of the MRI magnet, said method for constrained optimization design of the improved shim coil comprising the steps of:

generating the improved shim coil design suitable for fabrication which has at least one axial segment wherein each axial segment comprises a number of saddles distributed azimuthally;

using an expression $$V = -\int_S n(\rho, \phi, z) \frac{dB_{\perp np}^{mp}(\rho, \phi, z)}{dt} dA$$

to calculate a magnitude of a voltage V induced by the pulsed image gradient coils across terminals of the shim coil design, wherein $n(\rho,\phi,z)$ is the turns stream function and $B_{\perp np}^{mp}(\rho,\phi,z)$ is a component of a field due to only a primary harmonic generated by the pulsed imaging gradient coil that is perpendicular to a surface of said improved shim coil; and then constraining the magnitude of the induced voltage across the terminals of the improved shim coil design to be within a prescribed range of acceptable voltages, by selecting appropriate coil radial and axial positions $\rho_0(i),z_{01}(i)$ and $\rho_0(i),z_{02}(i)$ for each nseg segments comprising the improved shim coil, and for each segment selecting an appropriate set of magnitudes and signs for stream function weights $w(i, j)$ for $j=1$ to $j=j$ max and for $i=1$ to $i=$nseg.

7. The method recited by claim 6 wherein said prescribed range of acceptable voltages is greater than zero volts and less than 500 volts.

8. The method recited by claim 6 wherein said prescribed range of acceptable voltages is greater than zero volts and less than 100 volts.

9. The method recited by claim 6 wherein said prescribed range of acceptable voltages is from 25 volts to 75 volts.

10. The method recited by claim 6 further comprising an application without any knowledge of the configuration of electrical windings of the imaging gradient coil that is inducing that voltage.

11. An MR assembly comprising:
a series of X, Y and Z pulsed imaging gradient coils permanently arranged around a periphery of a bore of an MRI magnet in the MR assembly;
a portable shim insert configured for in-bore positioning inside a cavity space of the MRI Magnet;
the shim coil having reduced inductive coupling with the pulsed imaging gradient coils, the shim coil configured to provide a supplementary magnetic field gradient on-demand sufficient to reduce a high degree inhomogeneity of a primary magnetic B0 field present within the cavity space of the MRI magnet in the MR assembly; the shim coil including:
a set of nseg axially disposed segments, wherein each axial segment comprises a number of saddles distributed azimuthally;
a coil symmetry that is the same as the X, Y and Z pulsed imaging gradient coils permanently arranged around the periphery of the bore of an MRI magnet,
wherein a total induced voltage across the set of nseg segments comprising the shim coil is $$V = \frac{dG_x}{dt} \sum_{i=1}^{nseg} N(i)\rho_0(i)(z_{02}(i) - z_{01}(i)) \sum_{j=1}^{jmax} \frac{w(i, j)}{j}\left((-)^j z_{02}(i) - z_{01}(i)\right)$$

wherein $G_x$ is strength of the X pulsed imaged gradient and $N(i)$ is number of turns in a saddle of the $i^{th}$ axially disposed segment, and wherein a magnitude of the total induced voltage across terminals of the shim coil is constrained to lie within a predetermined range of voltage by selecting shim coil radial and axial positions $\rho_0(i),z_{01}(i)$ and $\rho_0(i),z_{02}(i)$ for each of the nseg segments comprising the shim coil, and for each segment selecting an appropriate set of magnitudes and signs for stream function weights $w(i, j)$ for $j=1$ to $j=j$ max and for $i=1$ to $i=$nseg.

12. The shim coil recited by claim 11 wherein said shim coil demonstrates at least one performance specification selected from the group consisting meeting strength requirements of a primary gradient while minimizing resistive power dissipation, limiting a deviation of a total field from a desired field, and minimizing a strength of specific spherical harmonic impurity fields.

13. The shim coil recited by claim 11 wherein said shim coil is configured to be placed in a central region of the X, Y and Z pulsed imaging gradient coils, includes an electrical conductor, is applied to a support structure, and is operative such that the induced voltage due to an imaging gradient coil that appears across terminals of said shim coil is less than a voltage compliance limit of a shim amplifier associated with that shim coil while presenting a resistance less than 4 ohms and inductance less than 10 millihenry.

14. The shim coil recited by claim 11 wherein said shim coil is comprised of circuits etched on a double sided printed circuit board.

15. The shim coil recited by claim 11 wherein said shim coil is composed of wire circuits.

16. An improved shim coil article comprising:
a designed shim coil having a capability of providing a supplementary magnetic field gradient on-demand sufficient to cancel a high degree inhomogeneity of the primary magnetic B0 field present within a cavity space of a MRI magnet in a MR assembly;
a set of nseg axially disposed segments, wherein each axial segment comprises a number of saddles distributed azimuthally;
a coil symmetry that is the same as X, Y and Z pulsed imaging gradient coils permanently arranged around a periphery of a bore of the MRI magnet;
the use of an expression $$V = \frac{dG_x}{dt} \sum_{i=1}^{nseg} N(i)\rho_0(i)(z_{02}(i) - z_{01}(i)) \sum_{j=1}^{jmax} \frac{w(i, j)}{j}\left((-)^j z_{02}(i) - z_{01}(i)\right)$$

to calculate a total induced voltage across the set of nseg segments comprising the designed shim coil, wherein $G_x$ is strength of the X pulsed imaged gradient and $N(i)$ is number of turns in a saddle of the $i^{th}$ axially disposed segment;
an effect of a constraint upon that total calculated induced voltage that will reduce a magnitude of the total induced voltage across terminals of the shim coil to lie within a prescribed range of acceptable voltages; and
a set of specifications for said designed shim coil having a constrained induced voltage which has fixed values for:
coordinates for positions of the axial segments $\rho_0(i),z_{01}(i)$ and $\rho_0(i),z_{02}(i)$, and the stream weight factors $w(j)$ for $j=1$ to $j=j$ max, and a numbers of turns in each segment $N(i)$.

17. The shim coil recited by claim 16 wherein said shim coil demonstrates at least one performance specification selected from the group consisting meeting the strength requirements of a primary gradient while minimizing resistive power dissipation, limiting a deviation of a total field from a desired field, and minimizing a strength of specific spherical harmonic impurity fields.

18. The shim coil recited by claim 16 wherein said shim coil is configured to be placed in a central region of the X, Y and Z pulsed imaging gradient coils, includes an electrical conductor, is applied to a support structure, and is operative such that the induced voltage due to an imaging gradient coil that appears across terminals of said shim coil is less than a voltage compliance limit of a shim amplifier associated with that shim coil while presenting a resistance less than 4 ohms and inductance less than 10 millihenry.

19. The shim coil recited by claim 16 wherein said shim coil is comprised of circuits etched on a double sided printed circuit board.

20. The shim coil recited by claim 16 wherein said shim coil is composed of wire circuits.

\* \* \* \* \*